US011700809B2

(12) United States Patent
Norsworthy et al.

(10) Patent No.: US 11,700,809 B2

(45) Date of Patent: Jul. 18, 2023

(54) HERBICIDE-RESISTANT GRAIN SORGHUM

(71) Applicants: THE BOARD OF TRUSTEES OF THE UNIVERSITY OF ARKANSAS, Little Rock, AR (US); THE TEXAS A&M UNIVERSITY SYSTEM, College Station, TX (US); The United Sorghum Checkoff Program Board, Lubbock, TX (US)

(72) Inventors: Jason Keith Norsworthy, West Fork, AR (US); Muthukumar Bagavathiannan, College Station, TX (US); William L. Rooney, College Station, TX (US); George L. Hodnett, College Station, TX (US)

(73) Assignees: The Board of Trustees of The University of Arkansas, Little Rock, AR (US); The Texas A&M University System, College Station, TX (US); The United Sorghum Checkoff Program Board, Lubbock, TX (US)

( * ) Notice: Subject to any disclaimer, the term of this patent is extended or adjusted under 35 U.S.C. 154(b) by 0 days.

(21) Appl. No.: 17/106,881

(22) Filed: Nov. 30, 2020

(65) Prior Publication Data

US 2021/0169030 A1 Jun. 10, 2021

Related U.S. Application Data

(60) Provisional application No. 62/943,663, filed on Dec. 4, 2019.

(51) Int. Cl.

*A01H 5/10* (2018.01)
*A01H 6/46* (2018.01)

(52) U.S. Cl.

CPC ............ *A01H 6/4666* (2018.05); *A01H 5/10* (2013.01)

(58) Field of Classification Search

CPC .................................................... A01H 6/4666
USPC .......................................................... 800/260
See application file for complete search history.

(56) References Cited

U.S. PATENT DOCUMENTS

| | | | | |
|---|---|---|---|---|
| 9,617,530 B2 | 4/2017 | Tuinstra | | |
| 2010/0205686 A1* | 8/2010 | Clement | ............. | A01H 6/4666 800/300 |
| 2017/0204429 A1 | 7/2017 | Tuinstra | | |
| 2018/0346920 A1 | 12/2018 | Nandakumar | | |

OTHER PUBLICATIONS

Bagavathiannan M, et al. (2018) Developing ACCase-inhibitor resistant grain sorghum. Presentation. Jan. 24, 2018. In Proceedings of the 2018 Southern Weed Science Society Annual Meeting, Atlanta, GA.
Besançon T, et al. (2017) Weed response to agronomic practices and herbicide strategies in grain sorghum. Agron J. 109:1642-1650.
Fromme DD, et al. (2012) Weed control and grain sorghum (Sorghum bicolor) tolerance to pyrasulotole plus bromoxynil. Int J Ag.
Heap I (2020) The international survey of herbicide resistant weeds. Retrieved Wednesday, Jan. 15, 2020 Available at www.weedscience.org.
Kaundun, S. S. “Resistance to acetyl-CoA carboxylase-inhibiting herbicides.” Pest Management Science 70.9 (2014): 1405-1417.
Kershner, K. S., et al. “Genetic resistance to acetyl-coenzyme A carboxylase-inhibiting herbicides in grain sorghum.” Crop science 52.1 (2012): 64-73.
Liu W, et al. (2007) Single-site mutations in the carboxyltransferase domain of plastid acetyl-CoA carboxylase confer resistance to grass-specific herbicides. PNAS. 104:3627-3632.
Werle R, et al. (2016) Distribution of herbicide-resistant shattercane and johnsongrass populations in sorghum production areas of Nebraska and northern Kansas. Agron J. 108:321-328.

* cited by examiner

*Primary Examiner* — Li Zheng
(74) *Attorney, Agent, or Firm* — Quarles & Brady LLP

(57) ABSTRACT

A fluazifop-resistant sorghum cultivar designated ‘21534_ACCase-R’ and plants comprising a polynucleotide encoding the polypeptide of SEQ ID NO: 39 are disclosed herein. The present invention provides seeds, plants, and plant parts derived from sorghum cultivar ‘21534_ACCase-R’ and those including SEQ ID NO: 39. Further, it provides methods for producing a sorghum plant by crossing ‘21534_ACCase-R’ with itself or another sorghum variety. The invention also encompasses any sorghum seeds, plants, and plant parts produced by the methods disclosed herein, including those in which additional traits have been transferred into ‘21534_ACCase-R’ through the introduction of a transgene or by breeding ‘21534_ACCase-R’ with another sorghum cultivar.

25 Claims, 21 Drawing Sheets

Specification includes a Sequence Listing.

Fig. 13 (continued)

Amino acid change (W to C) at position 2031 in Fluazifop-R sorghum, which corresponds to W2027C in blackgrass reference

B

```
Query  1921  PRAAIRGVDDSQGKWLGGMFDKDSFVETFEGWAKTVVTGRAKLGGIPVGVIAVETQTMMQ  1980
             PRAAIRGVDDSQGKWLGGMFDKDSFVETFEGWAKTVVTGRAKLGGIPVGVIAVETQTMMQ
Sbjct  1921  PRAAIRGVDDSQGKWLGGMFDKDSFVETFEGWAKTVVTGRAKLGGIPVGVIAVETQTMMQ  1980

Query  1981  LVPADPGQLDSHERSVPRAGQVWFPDSATKTAQALLDFNREGLPLFILANCRGFSGGQRD  2040
             LVPADPGQLDSHERSVPRAGQVWFPDSATKTAQALLDFNREGLPLFILAN RGFSGGQRD
Sbjct  1981  LVPADPGQLDSHERSVPRAGQVWFPDSATKTAQALLDFNREGLPLFILANWRGFSGGQRD  2040

Query  2041  LFEGILQAGSTIVENLRTYNQPAFVYIPMAGELRGGAWVVVDSKINPDRIECYAERTAKG  2100
             LFEGILQAGSTIVENLRTYNQPAFVYIPMAGELRGGAWVVVDSKINPDRIECYAERTAKG
Sbjct  2041  LFEGILQAGSTIVENLRTYNQPAFVYIPMAGELRGGAWVVVDSKINPDRIECYAERTAKG  2100

Query  2101  NVLEPQGLIEIKFRSEELQDCMGRLDPELINLKAKLQDVKHGNGSLPDIESLQKSIEART  2160
             NVLEPQGLIEIKFRSEELQDCMGRLDPELINLKAKLQDVKHGNGSLPDIESLQKSIEART
Sbjct  2101  NVLEPQGLIEIKFRSEELQDCMGRLDPELINLKAKLQDVKHGNGSLPDIESLQKSIEART  2160

Query  2161  KQLLPLYTQIAIRFAELHDTSLRMAAKGVIKKVVDWEESRSFFYKRLRRRISEDVLAKEI  2220
             KQLLPLYTQIAIRFAELHDTSLRMAAKGVIKKVVDWEESRSFFYKRLRRRISEDVLAKEI
Sbjct  2161  KQLLPLYTQIAIRFAELHDTSLRMAAKGVIKKVVDWEESRSFFYKRLRRRISEDVLAKEI  2220

Query  2221  RHIVGDNFTHQSAMELIKEWYLASPATAGSTGWDDDDAFVAWKDSPENYNGYIQELRAQK  2280
             RHIVGDNFTHQSAMELIKEWYLASPATAGSTGWDDDDAFVAWKDSPENYNGYIQELRAQK
Sbjct  2221  RHIVGDNFTHQSAMELIKEWYLASPATAGSTGWDDDDAFVAWKDSPENYNGYIQELRAQK  2280

Query  2281  VSQSLSDLTDSSSDLQAFSQGLSTLLDKMDPSQRAKFVQEVKKVLG  2326
             VSQSLSDLTDSSSDLQAFSQGLSTLLDKMDPSQRAKFVQEVKKVLG
Sbjct  2281  VSQSLSDLTDSSSDLQAFSQGLSTLLDKMDPSQRAKFVQEVKKVLG  2326
```

Query (SEQ ID NO:6) fluazifop-resistant sorghum
Subject (SEQ ID NO:7) wild-type sorghum

Amino acid change (A to T) at position
2248 in Fluazifop-R sorghum

```
Query  2161  KQLLPLYTQIAIRFAELHDTSLRMAAKGVIKKVVDWEESRSFFYKRLRRRISEDVLAKEI  2220
             KQLLPLYTQIAIRFAELHDTSLRMAAKGVIKKVVDWEESRSFFYKRLRRRISEDVLAKEI
Sbjct  2161  KQLLPLYTQIAIRFAELHDTSLRMAAKGVIKKVVDWEESRSFFYKRLRRRISEDVLAKEI  2220

Query  2221  RHIVGDNFTHQSAMELIKEWYLASPATTGSTGWDDDDAFVAWKDSPENYNGYIQELRAQK  2280
             RHIVGDNFTHQSAMELIKEWYLASPAT GSTGWDDDDAFVAWKDSPENYNGYIQELRAQK
Sbjct  2221  RHIVGDNFTHQSAMELIKEWYLASPATAGSTGWDDDDAFVAWKDSPENYNGYIQELRAQK  2280

Query  2281  VSQSLSDLTDSSSDLQAFSQGLSTLLDKMDPSQRAKFVQEVKKVLG  2326
             VSQSLSDLTDSSSDLQAFSQGLSTLLDKMDPSQRAKFVQEVKKVLG
Sbjct  2281  VSQSLSDLTDSSSDLQAFSQGLSTLLDKMDPSQRAKFVQEVKKVLG  2326
```

Query (SEQ ID NO:14) fluazifop-resistant sorghum
Subject (SEQ ID NO:15) wild-type sorghum

SEQUENCE LISTING

```
<160> NUMBER OF SEQ ID NOS: 39

<210> SEQ ID NO 1
<211> LENGTH: 359
<212> TYPE: DNA
<213> ORGANISM: Artificial Sequence
<220> FEATURE:
<223> OTHER INFORMATION: Synthetic- product amplified from the ACCase
      gene

<400> SEQUENCE: 1

tgatccagtc agcttgattc ccatgagcga tccgtcctcg ggctggacaa gtgtggttcc      60

cagattctgc aaccaagaca gctcaggcat tattagactt caaccgtgaa ggattgcctc     120

tgtttatcct ggctaactgc agaggtttct ctggtggaca gagagatctc tttgaaggaa     180

ttcttcaggc tgggtcaaca attgtcgaga accttaggac atataatcag cctgcgtttg     240

tctacattcc tatggctgga gagcttcgtg gaggagcttg ggttgtggtc gatagcaaaa     300

taaatccaga ccgcatcgag tgttatgctg agaggactgc caaaggtaat gttctcgaa      359


<210> SEQ ID NO 2
<211> LENGTH: 361
<212> TYPE: DNA
<213> ORGANISM: Artificial Sequence
<220> FEATURE:
<223> OTHER INFORMATION: Synthetic- product amplified from the ACCase
      gene

<400> SEQUENCE: 2

tgatccaggt cagcttgatt cccatgagcg atccgttcct cgggctggac aagtgtggtt      60

cccagattct gcaaccaaga cagctcaggc attattagac ttcaaccgtg aaggattgcc     120

tctgtttatc ctggctaact gcagaggttt ctctggtgga cagagagatc tctttgaagg     180

aattcttcag gctgggtcaa caattgtcga gaaccttagg acatataatc agcctgcgtt     240

tgtctacatt cctatggctg gagagcttcg tggaggagct tgggttgtgg tcgatagcaa     300

aataaatcca gaccgcatcg agtgttatgc tgagaggact gccaaaggta atgttctcga     360

a                                                                     361


<210> SEQ ID NO 3
<211> LENGTH: 361
<212> TYPE: DNA
<213> ORGANISM: Artificial Sequence
<220> FEATURE:
<223> OTHER INFORMATION: Synthetic- product amplified from the ACCase
      gene

<400> SEQUENCE: 3

tgatccaggt cagcttgatt cccatgagcg atccgttcct cgggctggac aagtgtggtt      60

cccagattct gcaaccaaga cagctcaggc attattagac ttcaaccgtg aaggattgcc     120

tctgtttatc ctggctaact gcagaggttt ctctggtgga cagagagatc tctttgaagg     180

aattcttcag gctgggtcaa caattgtcga gaaccttagg acatataatc agcctgcgtt     240
```

-continued

```
tgtctacatt cctatggctg gagagcttcg tggaggagct tgggttgtgg tcgatagcaa    300

aataaatcca gaccgcatcg agtgttatgc tgagaggact gccaaaggta atgttctcga    360

a                                                                    361


<210> SEQ ID NO 4
<211> LENGTH: 361
<212> TYPE: DNA
<213> ORGANISM: Artificial Sequence
<220> FEATURE:
<223> OTHER INFORMATION: Synthetic- product amplified from the ACCase
      gene

<400> SEQUENCE: 4

tgatccaggt cagcttgatt cccatgagcg atccgttcct cgggctggac aagtgtggtt     60

cccagattct gcaaccaaga cagctcaggc attattagac ttcaaccgtg aaggattgcc    120

tctgtttatc ctggctaact gcagaggttt ctctggtgga cagagagatc tctttgaagg    180

aattcttcag gctgggtcaa caattgtcga gaaccttagg acatataatc agcctgcgtt    240

tgtctacatt cctatggctg gagagcttcg tggaggagct tgggttgtgg tcgatagcaa    300

aataaatcca gaccgcatcg agtgttatgc tgagaggact gccaaaggta atgttctcga    360

a                                                                    361


<210> SEQ ID NO 5
<211> LENGTH: 361
<212> TYPE: DNA
<213> ORGANISM: Artificial Sequence
<220> FEATURE:
<223> OTHER INFORMATION: Synthetic- product amplified from the ACCase
      gene

<400> SEQUENCE: 5

tgatccaggt cagcttgatt cccatgagcg atccgttcct cgggctggac aagtgtggtt     60

cccagattct gcaaccaaga cagctcaggc attattagac ttcaaccgtg aaggattgcc    120

tctgtttatc ctggctaact ggagaggttt ctctggtgga cagagagatc tctttgaagg    180

aattcttcag gctgggtcaa caattgtcga gaaccttagg acatataatc agcctgcgtt    240

tgtctacatt cctatggctg gagagcttcg tggaggagct tgggttgtgg tcgatagcaa    300

aataaatcca gaccgcattg agtgttatgc tgagaggact gccaaaggta atgttctcga    360

a                                                                    361


<210> SEQ ID NO 6
<211> LENGTH: 406
<212> TYPE: PRT
<213> ORGANISM: Artificial Sequence
<220> FEATURE:
<223> OTHER INFORMATION: Synthetic- product amplified from the ACCase
      gene

<400> SEQUENCE: 6

Pro Arg Ala Ala Ile Arg Gly Val Asp Asp Ser Gln Gly Lys Trp Leu
1               5                   10                  15

Gly Gly Met Phe Asp Lys Asp Ser Phe Val Glu Thr Phe Glu Gly Trp
            20                  25                  30

Ala Lys Thr Val Val Thr Gly Arg Ala Lys Leu Gly Gly Ile Pro Val
        35                  40                  45

Gly Val Ile Ala Val Glu Thr Gln Thr Met Met Gln Leu Val Pro Ala
    50                  55                  60
```

-continued

Asp Pro Gly Gln Leu Asp Ser His Glu Arg Ser Val Pro Arg Ala Gly
65 70 75 80

Gln Val Trp Phe Pro Asp Ser Ala Thr Lys Thr Ala Gln Ala Leu Leu
85 90 95

Asp Phe Asn Arg Glu Gly Leu Pro Leu Phe Ile Leu Ala Asn Cys Arg
100 105 110

Gly Phe Ser Gly Gly Gln Arg Asp Leu Phe Glu Gly Ile Leu Gln Ala
115 120 125

Gly Ser Thr Ile Val Glu Asn Leu Arg Thr Tyr Asn Gln Pro Ala Phe
130 135 140

Val Tyr Ile Pro Met Ala Gly Glu Leu Arg Gly Gly Ala Trp Val Val
145 150 155 160

Val Asp Ser Lys Ile Asn Pro Asp Arg Ile Glu Cys Tyr Ala Glu Arg
165 170 175

Thr Ala Lys Gly Asn Val Leu Glu Pro Gln Gly Leu Ile Glu Ile Lys
180 185 190

Phe Arg Ser Glu Glu Leu Gln Asp Cys Met Gly Arg Leu Asp Pro Glu
195 200 205

Leu Ile Asn Leu Lys Ala Lys Leu Gln Asp Val Lys His Gly Asn Gly
210 215 220

Ser Leu Pro Asp Ile Glu Ser Leu Gln Lys Ser Ile Glu Ala Arg Thr
225 230 235 240

Lys Gln Leu Leu Pro Leu Tyr Thr Gln Ile Ala Ile Arg Phe Ala Glu
245 250 255

Leu His Asp Thr Ser Leu Arg Met Ala Ala Lys Gly Val Ile Lys Lys
260 265 270

Val Val Asp Trp Glu Glu Ser Arg Ser Phe Phe Tyr Lys Arg Leu Arg
275 280 285

Arg Arg Ile Ser Glu Asp Val Leu Ala Lys Glu Ile Arg His Ile Val
290 295 300

Gly Asp Asn Phe Thr His Gln Ser Ala Met Glu Leu Ile Lys Glu Trp
305 310 315 320

Tyr Leu Ala Ser Pro Ala Thr Thr Gly Ser Thr Gly Trp Asp Asp Asp
325 330 335

Asp Ala Phe Val Ala Trp Lys Asp Ser Pro Glu Asn Tyr Asn Gly Tyr
340 345 350

Ile Gln Glu Leu Arg Ala Gln Lys Val Ser Gln Ser Leu Ser Asp Leu
355 360 365

Thr Asp Ser Ser Ser Asp Leu Gln Ala Phe Ser Gln Gly Leu Ser Thr
370 375 380

Leu Leu Asp Lys Met Asp Pro Ser Gln Arg Ala Lys Phe Val Gln Glu
385 390 395 400

Val Lys Lys Val Leu Gly
405

<210> SEQ ID NO 7
<211> LENGTH: 406
<212> TYPE: PRT
<213> ORGANISM: Artificial Sequence
<220> FEATURE:
<223> OTHER INFORMATION: Synthetic- product amplified from the ACCase gene

<400> SEQUENCE: 7

Pro Arg Ala Ala Ile Arg Gly Val Asp Asp Ser Gln Gly Lys Trp Leu
1 5 10 15

-continued

```
Gly Gly Met Phe Asp Lys Asp Ser Phe Val Glu Thr Phe Glu Gly Trp
            20                  25                  30

Ala Lys Thr Val Val Thr Gly Arg Ala Lys Leu Gly Gly Ile Pro Val
        35                  40                  45

Gly Val Ile Ala Val Glu Thr Gln Thr Met Met Gln Leu Val Pro Ala
    50                  55                  60

Asp Pro Gly Gln Leu Asp Ser His Glu Arg Ser Val Pro Arg Ala Gly
65                  70                  75                  80

Gln Val Trp Phe Pro Asp Ser Ala Thr Lys Thr Ala Gln Ala Leu Leu
                85                  90                  95

Asp Phe Asn Arg Glu Gly Leu Pro Leu Phe Ile Leu Ala Asn Trp Arg
            100                 105                 110

Gly Phe Ser Gly Gly Gln Arg Asp Leu Phe Glu Gly Ile Leu Gln Ala
        115                 120                 125

Gly Ser Thr Ile Val Glu Asn Leu Arg Thr Tyr Asn Gln Pro Ala Phe
    130                 135                 140

Val Tyr Ile Pro Met Ala Gly Glu Leu Arg Gly Gly Ala Trp Val Val
145                 150                 155                 160

Val Asp Ser Lys Ile Asn Pro Asp Arg Ile Glu Cys Tyr Ala Glu Arg
                165                 170                 175

Thr Ala Lys Gly Asn Val Leu Glu Pro Gln Gly Leu Ile Glu Ile Lys
            180                 185                 190

Phe Arg Ser Glu Glu Leu Gln Asp Cys Met Gly Arg Leu Asp Pro Glu
        195                 200                 205

Leu Ile Asn Leu Lys Ala Lys Leu Gln Asp Val Lys His Gly Asn Gly
    210                 215                 220

Ser Leu Pro Asp Ile Glu Ser Leu Gln Lys Ser Ile Glu Ala Arg Thr
225                 230                 235                 240

Lys Gln Leu Leu Pro Leu Tyr Thr Gln Ile Ala Ile Arg Phe Ala Glu
                245                 250                 255

Leu His Asp Thr Ser Leu Arg Met Ala Ala Lys Gly Val Ile Lys Lys
            260                 265                 270

Val Val Asp Trp Glu Glu Ser Arg Ser Phe Phe Tyr Lys Arg Leu Arg
        275                 280                 285

Arg Arg Ile Ser Glu Asp Val Leu Ala Lys Glu Ile Arg His Ile Val
    290                 295                 300

Gly Asp Asn Phe Thr His Gln Ser Ala Met Glu Leu Ile Lys Glu Trp
305                 310                 315                 320

Tyr Leu Ala Ser Pro Ala Thr Thr Gly Ser Thr Gly Trp Asp Asp Asp
                325                 330                 335

Asp Ala Phe Val Ala Trp Lys Asp Ser Pro Glu Asn Tyr Asn Gly Tyr
            340                 345                 350

Ile Gln Glu Leu Arg Ala Gln Lys Val Ser Gln Ser Leu Ser Asp Leu
        355                 360                 365

Thr Asp Ser Ser Ser Asp Leu Gln Ala Phe Ser Gln Gly Leu Ser Thr
    370                 375                 380

Leu Leu Asp Lys Met Asp Pro Ser Gln Arg Ala Lys Phe Val Gln Glu
385                 390                 395                 400

Val Lys Lys Val Leu Gly
                405
```

<210> SEQ ID NO 8
<211> LENGTH: 618

<212> TYPE: DNA
<213> ORGANISM: Artificial Sequence
<220> FEATURE:
<223> OTHER INFORMATION: Synthetic- product amplified from the ACCase
      gene

<400> SEQUENCE: 8

```
gaggactgcc aaaggtaatg ttctcgaacc tcaagggtta attgaaatca agttcaggtc     60

agaggaactc caagactgta tgggtaggct tgacccggag ttgataaatc tgaaagcaaa    120

actccaagat gtaaagcatg gaaatggaag tctaccagac atagaatccc ttcagaagag    180

tatagaagca cgtacgaaac agttgctgcc tttatatacc cagattgcaa tacggtttgc    240

tgaattgcat gatacttccc taagaatggc agctaaaggc gtgattaaga aagttgtaga    300

ctgggaagaa tcacgctctt tcttctataa aaggctacgg agaaggatct ctgaagatgt    360

tcttgcaaaa gaaataagac atatagtcgg tgacaacttc actcaccaat cagcaatgga    420

gctcatcaag gaatggtacc tggcttctcc agccacaaca ggaagcactg gatgggatga    480

cgatgatgca tttgttgcct ggaaggacag tcctgaaaac tacaatggat atatccaaga    540

gctaagggct caaaaagtgt ctcagtcgct ctctgatctc actgactcca gttcagatct    600

acaagcattc tcgcaggg                                                  618
```

<210> SEQ ID NO 9
<211> LENGTH: 618
<212> TYPE: DNA
<213> ORGANISM: Artificial Sequence
<220> FEATURE:
<223> OTHER INFORMATION: Synthetic- product amplified from the ACCase
      gene

<400> SEQUENCE: 9

```
gaggactgcc aaaggtaatg ttctcgaacc tcaagggtta attgaaatca agttcaggtc     60

agaggaactc caagactgta tgggtaggct tgacccggag ttgataaatc tgaaagcaaa    120

actccaagat gtaaagcatg gaaatggaag tctaccagac atagaatccc ttcagaagag    180

tatagaagca cgtacgaaac agttgctgcc tttatatacc cagattgcaa tacggtttgc    240

tgaattgcat gatacttccc taagaatggc agctaaaggc gtgattaaga aagttgtaga    300

ctgggaagaa tcacgctctt tcttctataa aaggctacgg agaaggatct ctgaagatgt    360

tcttgcaaaa gaaataagac atatagtcgg tgacaacttc actcaccaat cagcaatgga    420

gctcatcaag gaatggtacc tggcttctcc agccacaaca ggaagcactg gatgggatga    480

cgatgatgca tttgttgcct ggaaggacag tcctgaaaac tacaatggat atatccaaga    540

gctaagggct caaaaagtgt ctcagtcgct ctctgatctc actgactcca gttcagatct    600

acaagcattc tcgcaggg                                                  618
```

<210> SEQ ID NO 10
<211> LENGTH: 618
<212> TYPE: DNA
<213> ORGANISM: Artificial Sequence
<220> FEATURE:
<223> OTHER INFORMATION: Synthetic- product amplified from the ACCase
      gene

<400> SEQUENCE: 10

```
gaggactgcc aaaggtaatg ttctcgaacc tcaagggtta attgaaatca agttcaggtc     60

agaggaactc caagactgta tgggtaggct tgacccggag ttgataaatc tgaaagcaaa    120

actccaagat gtaaagcatg gaaatggaag tctaccagac atagaatccc ttcagaagag    180
```

-continued tatagaagca cgtacgaaac agttgctgcc tttatatacc cagattgcaa tacggtttgc 240
tgaattgcat gatacttccc taagaatggc agctaaaggc gtgattaaga aagttgtaga 300
ctgggaagaa tcacgctctt tcttctataa aaggctacgg agaaggatct ctgaagatgt 360
tcttgcaaaa gaaataagac atatagtcgg tgacaacttc actcaccaat cagcaatgga 420
gctcatcaag gaatggtacc tggcttctcc agccacaaca ggaagcactg gatgggatga 480
cgatgatgca tttgttgcct ggaaggacag tcctgaaaac tacaatggat atatccaaga 540
gctaagggct caaaaagtgt ctcagtcgct ctctgatctc actgactcca gttcagatct 600
acaagcattc tcgcaggg 618

<210> SEQ ID NO 11
<211> LENGTH: 564
<212> TYPE: DNA
<213> ORGANISM: Artificial Sequence
<220> FEATURE:
<223> OTHER INFORMATION: Synthetic- product amplified from the ACCase gene

<400> SEQUENCE: 11
caggtcagag gaactccaag actgtatggg taggcttgac ccggagttga taaatctgaa 60
agcaaaactc caagatgtaa agcatggaaa tggaagtcta ccagacatag aatcccttca 120
gaagagtata gaagcacgta cgaaacagtt gctgccttta tatacccaga ttgcaatacg 180
gtttgctgaa ttgcatgata cttccctaag aatggcagct aaaggcgtga ttaagaaagt 240
tgtagactgg gaagaatcac gctctttctt ctataaaagg ctacggagaa ggatctctga 300
agatgttctt gcaaaagaaa taagacatat agtcggtgac aacttcactc accaatcagc 360
aatggagctc atcaaggaat ggtacctggc ttctccagcc acaacaggaa gcactggatg 420
ggatgacgat gatgcatttg ttgcctggaa ggacagtcct gaaaactaca atggatatat 480
ccaagagcta agggctcaaa aagtgtctca gtcgctctct gatctcactg actccagttc 540
agatctacaa gcattctcgc aggg 564

<210> SEQ ID NO 12
<211> LENGTH: 571
<212> TYPE: DNA
<213> ORGANISM: Artificial Sequence
<220> FEATURE:
<223> OTHER INFORMATION: Synthetic- product amplified from the ACCase gene

<400> SEQUENCE: 12
gaggactgcc aaaggtaatg ttctcgaacc tcaagggtta attgaaatca agttcaggtc 60
agaggaactc caaactgtat gggtaggctt gacccggagt tgataaatct gaaagcaaaa 120
ctccaagatg taaagcatgg aaatggaagt ctaccagaca tagaatccct tcagaagagt 180
atagaagcac gtacgaaaca gttgctgcct ttatataccc agattgcaat acggtttgct 240
gaattgcatg atacttccct aagaatggca gctaaaggcg tgattaagaa agttgtagac 300
tgggaagaat cacgctcttt cttctataaa aggctacgga gaaggatctc tgaagatgtt 360
cttgcaaaag aaataagaca tatagtcggt gacaacttca ctcaccaatc agcaatggag 420
ctcatcaagg aatggtacct ggcttctcca gccacaacag gaagcactgg atgggatgac 480
gatgatgcat ttgttgcctg gaaggacagt cctgaaaact acaatggata tatccaagag 540
ctaagggctc aaaaagtgtc tcagtcgctc t 571

<210> SEQ ID NO 13
<211> LENGTH: 618
<212> TYPE: DNA
<213> ORGANISM: Artificial Sequence
<220> FEATURE:
<223> OTHER INFORMATION: Synthetic- product amplified from the ACCase gene

<400> SEQUENCE: 13
gaggactgcc aaaggtaatg ttctcgaacc tcaagggtta attgaaatca agttcaggtc 60
agaggaactc caagactgta tgggtaggct tgaccccgag ttgataaatc tgaaagcaaa 120
actccaagat gtaaagcatg gaaatggaag tctaccagac atagaatccc ttcagaagag 180
tatagaagca cgtacgaaac agttgctgcc tttatatacc cagattgcaa tacggtttgc 240
tgaattgcat gatacttccc taagaatggc agctaaaggc gtgattaaga aagttgtaga 300
ctgggaagaa tcacgctctt tcttctataa aaggctacgg agaaggatct ctgaagatgt 360
tcttgcaaaa gaaataagac atatagtcgg tgacaacttc actcaccaat cagcaatgga 420
gctcatcaag gaatggtacc tggcttctcc agccacagca ggaagcactg gatgggatga 480
cgatgatgca tttgttgcct ggaaggacag tcctgaaaac tacaatggat atatccaaga 540
gctaagggct caaaaagtgt ctcagtcgct ctctgatctc actgactcca gttcagatct 600
acaagcattc tcgcaggg 618

<210> SEQ ID NO 14
<211> LENGTH: 166
<212> TYPE: PRT
<213> ORGANISM: Artificial Sequence
<220> FEATURE:
<223> OTHER INFORMATION: Synthetic- product amplified from the ACCase gene

<400> SEQUENCE: 14

```
Lys Gln Leu Leu Pro Leu Tyr Thr Gln Ile Ala Ile Arg Phe Ala Glu
1               5                   10                  15

Leu His Asp Thr Ser Leu Arg Met Ala Ala Lys Gly Val Ile Lys Lys
            20                  25                  30

Val Val Asp Trp Glu Glu Ser Arg Ser Phe Phe Tyr Lys Arg Leu Arg
        35                  40                  45

Arg Arg Ile Ser Glu Asp Val Leu Ala Lys Glu Ile Arg His Ile Val
    50                  55                  60

Gly Asp Asn Phe Thr His Gln Ser Ala Met Glu Leu Ile Lys Glu Trp
65                  70                  75                  80

Tyr Leu Ala Ser Pro Ala Thr Thr Gly Ser Thr Gly Trp Asp Asp Asp
                85                  90                  95

Asp Ala Phe Val Ala Trp Lys Asp Ser Pro Glu Asn Tyr Asn Gly Tyr
            100                 105                 110

Ile Gln Glu Leu Arg Ala Gln Lys Val Ser Gln Ser Leu Ser Asp Leu
        115                 120                 125

Thr Asp Ser Ser Ser Asp Leu Gln Ala Phe Ser Gln Gly Leu Ser Thr
    130                 135                 140

Leu Leu Asp Lys Met Asp Pro Ser Gln Arg Ala Lys Phe Val Gln Glu
145                 150                 155                 160

Val Lys Lys Val Leu Gly
                165
```

<210> SEQ ID NO 15

<211> LENGTH: 166
<212> TYPE: PRT
<213> ORGANISM: Artificial Sequence
<220> FEATURE:
<223> OTHER INFORMATION: Synthetic- product amplified from the ACCase gene

<400> SEQUENCE: 15

```
Lys Gln Leu Leu Pro Leu Tyr Thr Gln Ile Ala Ile Arg Phe Ala Glu
1               5                   10                  15

Leu His Asp Thr Ser Leu Arg Met Ala Ala Lys Gly Val Ile Lys Lys
            20                  25                  30

Val Val Asp Trp Glu Glu Ser Arg Ser Phe Phe Tyr Lys Arg Leu Arg
        35                  40                  45

Arg Arg Ile Ser Glu Asp Val Leu Ala Lys Glu Ile Arg His Ile Val
    50                  55                  60

Gly Asp Asn Phe Thr His Gln Ser Ala Met Glu Leu Ile Lys Glu Trp
65                  70                  75                  80

Tyr Leu Ala Ser Pro Ala Thr Ala Gly Ser Thr Gly Trp Asp Asp Asp
                85                  90                  95

Asp Ala Phe Val Ala Trp Lys Asp Ser Pro Glu Asn Tyr Asn Gly Tyr
            100                 105                 110

Ile Gln Glu Leu Arg Ala Gln Lys Val Ser Gln Ser Leu Ser Asp Leu
        115                 120                 125

Thr Asp Ser Ser Ser Asp Leu Gln Ala Phe Ser Gln Gly Leu Ser Thr
    130                 135                 140

Leu Leu Asp Lys Met Asp Pro Ser Gln Arg Ala Lys Phe Val Gln Glu
145                 150                 155                 160

Val Lys Lys Val Leu Gly
                165
```

<210> SEQ ID NO 16
<211> LENGTH: 80
<212> TYPE: DNA
<213> ORGANISM: Artificial Sequence
<220> FEATURE:
<223> OTHER INFORMATION: Synthetic- product amplified from the ACCase gene

<400> SEQUENCE: 16

```
cagcaatgga gctcatcaag gaatggtacc tggcttctcc agccacaaca ggaagcactg     60

gatgggatga cgatgatgca                                                 80
```

<210> SEQ ID NO 17
<211> LENGTH: 27
<212> TYPE: PRT
<213> ORGANISM: Artificial Sequence
<220> FEATURE:
<223> OTHER INFORMATION: Synthetic- product amplified from the ACCase gene

<400> SEQUENCE: 17

```
Ser Ala Met Glu Leu Ile Lys Glu Trp Tyr Leu Ala Ser Pro Ala Thr
1               5                   10                  15

Thr Gly Ser Thr Gly Trp Asp Asp Asp Asp Ala
            20                  25
```

<210> SEQ ID NO 18
<211> LENGTH: 27
<212> TYPE: PRT
<213> ORGANISM: Artificial Sequence

```
<220> FEATURE:
<223> OTHER INFORMATION: Synthetic- product amplified from the ACCase
      gene

<400> SEQUENCE: 18

Ser Ala Met Glu Leu Ile Lys Glu Trp Tyr Leu Ala Ser Pro Ala Thr
1               5                   10                  15

Thr Gly Ser Thr Gly Trp Asp Asp Asp Asp Ala
            20                  25


<210> SEQ ID NO 19
<211> LENGTH: 27
<212> TYPE: PRT
<213> ORGANISM: Artificial Sequence
<220> FEATURE:
<223> OTHER INFORMATION: Synthetic- product amplified from the ACCase
      gene

<400> SEQUENCE: 19

Ser Ala Met Glu Leu Ile Lys Glu Trp Tyr Leu Ala Ser Pro Ala Thr
1               5                   10                  15

Thr Gly Ser Thr Gly Trp Asp Asp Asp Asp Ala
            20                  25


<210> SEQ ID NO 20
<211> LENGTH: 27
<212> TYPE: PRT
<213> ORGANISM: Artificial Sequence
<220> FEATURE:
<223> OTHER INFORMATION: Synthetic- product amplified from the ACCase
      gene

<400> SEQUENCE: 20

Ser Ala Met Glu Leu Ile Lys Glu Trp Tyr Leu Ala Ser Pro Ala Thr
1               5                   10                  15

Ala Gly Ser Thr Gly Trp Asp Asp Asp Asp Ala
            20                  25


<210> SEQ ID NO 21
<211> LENGTH: 27
<212> TYPE: PRT
<213> ORGANISM: Artificial Sequence
<220> FEATURE:
<223> OTHER INFORMATION: Synthetic- product amplified from the ACCase
      gene

<400> SEQUENCE: 21

Ser Ala Met Glu Leu Ile Lys Glu Trp Tyr Leu Ala Ser Pro Ala Thr
1               5                   10                  15

Ala Gly Ser Thr Gly Trp Asp Asp Asp Asp Ala
            20                  25


<210> SEQ ID NO 22
<211> LENGTH: 27
<212> TYPE: PRT
<213> ORGANISM: Artificial Sequence
<220> FEATURE:
<223> OTHER INFORMATION: Synthetic- product amplified from the ACCase
      gene

<400> SEQUENCE: 22

Ser Ala Met Glu Leu Ile Lys Glu Trp Tyr Leu Ala Ser Pro Ala Thr
1               5                   10                  15

Ala Gly Ser Thr Gly Trp Asp Asp Asp Asp Ala
            20                  25
```

<210> SEQ ID NO 23
<211> LENGTH: 27
<212> TYPE: PRT
<213> ORGANISM: Artificial Sequence
<220> FEATURE:
<223> OTHER INFORMATION: Synthetic- product amplified from the ACCase gene

<400> SEQUENCE: 23

```
Ser Ala Met Glu Leu Ile Lys Glu Trp Tyr Leu Ala Ser Pro Ala Thr
1               5                   10                  15

Thr Gly Ser Thr Gly Trp Asp Asp Asp Asp Ala
            20                  25
```

<210> SEQ ID NO 24
<211> LENGTH: 27
<212> TYPE: PRT
<213> ORGANISM: Artificial Sequence
<220> FEATURE:
<223> OTHER INFORMATION: Synthetic- product amplified from the ACCase gene

<400> SEQUENCE: 24

```
Ser Ala Met Glu Leu Ile Lys Glu Trp Tyr Leu Ala Ser Pro Ala Thr
1               5                   10                  15

Thr Gly Ser Thr Gly Trp Asp Asp Asp Asp Ala
            20                  25
```

<210> SEQ ID NO 25
<211> LENGTH: 27
<212> TYPE: PRT
<213> ORGANISM: Artificial Sequence
<220> FEATURE:
<223> OTHER INFORMATION: Synthetic- product amplified from the ACCase gene

<400> SEQUENCE: 25

```
Ser Ala Met Glu Leu Ile Lys Glu Trp Tyr Leu Ala Ser Pro Ala Thr
1               5                   10                  15

Thr Gly Ser Thr Gly Trp Asp Asp Asp Asp Ala
            20                  25
```

<210> SEQ ID NO 26
<211> LENGTH: 20
<212> TYPE: DNA
<213> ORGANISM: Artificial Sequence
<220> FEATURE:
<223> OTHER INFORMATION: Synthetic- primer for amplification of the ACCase gene

<400> SEQUENCE: 26

```
tgcagctaga tagcggtgaa                                                20
```

<210> SEQ ID NO 27
<211> LENGTH: 20
<212> TYPE: DNA
<213> ORGANISM: Artificial Sequence
<220> FEATURE:
<223> OTHER INFORMATION: Synthetic- primer for amplification of the ACCase gene

<400> SEQUENCE: 27

```
ttatcaactc ggggtcaagc                                                20
```

-continued

<210> SEQ ID NO 28
<211> LENGTH: 20
<212> TYPE: DNA
<213> ORGANISM: Artificial Sequence
<220> FEATURE:
<223> OTHER INFORMATION: Synthetic- primer for amplification of the ACCase gene

<400> SEQUENCE: 28
ttgtccctgc tgatccaggt 20

<210> SEQ ID NO 29
<211> LENGTH: 20
<212> TYPE: DNA
<213> ORGANISM: Artificial Sequence
<220> FEATURE:
<223> OTHER INFORMATION: Synthetic- primer for amplification of the ACCase gene

<400> SEQUENCE: 29
aacccttgag gttcgagaac 20

<210> SEQ ID NO 30
<211> LENGTH: 20
<212> TYPE: DNA
<213> ORGANISM: Artificial Sequence
<220> FEATURE:
<223> OTHER INFORMATION: Synthetic- primer for amplification of the ACCase gene

<400> SEQUENCE: 30
tgttgggtgg tctgacgaag 20

<210> SEQ ID NO 31
<211> LENGTH: 20
<212> TYPE: DNA
<213> ORGANISM: Artificial Sequence
<220> FEATURE:
<223> OTHER INFORMATION: Synthetic- primer for amplification of the ACCase gene

<400> SEQUENCE: 31
cacgtggatc gcatgtgttc 20

<210> SEQ ID NO 32
<211> LENGTH: 20
<212> TYPE: DNA
<213> ORGANISM: Artificial Sequence
<220> FEATURE:
<223> OTHER INFORMATION: Synthetic- primer for amplification of the ACCase gene

<400> SEQUENCE: 32
tggctcagct atgttcctgc 20

<210> SEQ ID NO 33
<211> LENGTH: 20
<212> TYPE: DNA
<213> ORGANISM: Artificial Sequence
<220> FEATURE:
<223> OTHER INFORMATION: Synthetic- primer for amplification of the ACCase gene

<400> SEQUENCE: 33
ggcagcaact gtttcgtacg 20

<210> SEQ ID NO 34

<211> LENGTH: 23
<212> TYPE: DNA
<213> ORGANISM: Artificial Sequence
<220> FEATURE:
<223> OTHER INFORMATION: Synthetic- primer for amplification of the
ACCase gene

<400> SEQUENCE: 34
gaagaagact atgcccgtat tag 23

<210> SEQ ID NO 35
<211> LENGTH: 21
<212> TYPE: DNA
<213> ORGANISM: Artificial Sequence
<220> FEATURE:
<223> OTHER INFORMATION: Synthetic- primer for amplification of the
ACCase gene

<400> SEQUENCE: 35
cctctgacct gaacttgatt t 21

<210> SEQ ID NO 36
<211> LENGTH: 20
<212> TYPE: DNA
<213> ORGANISM: Artificial Sequence
<220> FEATURE:
<223> OTHER INFORMATION: Synthetic- primer for amplification of the
ACCase gene

<400> SEQUENCE: 36
gaggactgcc aaaggtaatg 20

<210> SEQ ID NO 37
<211> LENGTH: 19
<212> TYPE: DNA
<213> ORGANISM: Artificial Sequence
<220> FEATURE:
<223> OTHER INFORMATION: Synthetic- primer for amplification of the
ACCase gene

<400> SEQUENCE: 37
gaaagaccct gcgagaatg 19

<210> SEQ ID NO 38
<211> LENGTH: 1658
<212> TYPE: DNA
<213> ORGANISM: Sorghum bicolor
<220> FEATURE:
<221> NAME/KEY: misc_feature
<222> LOCATION: (1)..(1658)
<223> OTHER INFORMATION: Consensus ACCase nucleotide sequence in
fluazifop-resistant sorghum plant

<400> SEQUENCE: 38
gtattagctc ttctgttata gcacataagc tgcagctaga tagcggtgaa attaggtgga 60
ttattgactc tgttgtgggc aaggaggatg ggcttggtgt tgagaacata catggaagtg 120
ctgctatcgc cagtgcttat tctagggcat atgaggagac atttacactt acatttgtga 180
ccggacggac tgtaggaata ggagcttatc ttgctagact tggtatacgg tgcatacagc 240
gtcttgacca gccgattatt ttaacagggt tttctgccct gaacaagctc cttgggcggg 300
aagtgtacag ctcccacatg cagcttggtg gtcctaagat catggcgacc aatggtgttg 360
tccacctgac tgttccagat gaccttgaag gtgtttccaa tatattgagg tggctcagct 420
atgttcctgc aaacattggt ggacctcttc ctattaccaa acctttggac cctccagaca 480

-continued

```
gacctgttgc atacatccct gagaacacat gcgatccacg tgcagccatc cgtggtgtag    540

atgacagcca agggaaatgg ttgggtggta tgtttgacaa agacagcttt gtggagacat    600

ttgaaggatg ggcaaaaaca gtggttactg gcagagcaaa gcttggagga attcctgtgg    660

gtgtcatagc tgtggagaca cagaccatga tgcagcttgt ccctgctgat ccaggtcagc    720

ttgattccca tgagcgatcc gttcctcggg ctggacaagt gtggttccca gattctgcaa    780

ccaagacagc tcaggcatta ttagacttca accgtgaagg attgcctctg tttatcctgg    840

ctaactgcag aggtttctct ggtggacaga gagatctctt tgaaggaatt cttcaggctg    900

ggtcaacaat tgtcgagaac cttaggacat ataatcagcc tgcgtttgtc tacattccta    960

tggctggaga gcttcgtgga ggagcttggg ttgtggtcga tagcaaaata aatccagacc   1020

gcatcgagtg ttatgctgag aggactgcca aaggtaatgt tctcgaacct caagggttaa   1080

ttgaaatcaa gttcaggtca gaggaactcc aagactgtat gggtaggctt gacccggagt   1140

tgataaatct gaaagcaaaa ctccaagatg taaagcatgg aaatggaagt ctaccagaca   1200

tagaatccct tcagaagagt atagaagcac gtacgaaaca gttgctgcct ttatataccc   1260

agattgcaat acggtttgct gaattgcatg atacttccct aagaatggca gctaaaggcg   1320

tgattaagaa agttgtagac tgggaagaat cacgctcttt cttctataaa aggctacgga   1380

gaaggatctc tgaagatgtt cttgcaaaag aaataagaca tatagtcggt gacaacttca   1440

ctcaccaatc agcaatggag ctcatcaagg aatggtacct ggcttctcca gccacaacag   1500

gaagcactgg atgggatgac gatgatgcat ttgttgcctg gaaggacagt cctgaaaact   1560

acaatggata tatccaagag ctaagggctc aaaaagtgtc tcagtcgctc tctgatctca   1620

ctgactccag ttcagatcta caagcattct cgcagggg                           1658
```

```
<210> SEQ ID NO 39
<211> LENGTH: 552
<212> TYPE: PRT
<213> ORGANISM: Sorghum bicolor
<220> FEATURE:
<221> NAME/KEY: MISC_FEATURE
<222> LOCATION: (1)..(552)
<223> OTHER INFORMATION: Consensus ACCase protein sequence in fluazifop-
      resistant sorghum plant

<400> SEQUENCE: 39

Ile Ser Ser Ser Val Ile Ala His Lys Leu Gln Leu Asp Ser Gly Glu
1               5                   10                  15

Ile Arg Trp Ile Ile Asp Ser Val Val Gly Lys Glu Asp Gly Leu Gly
            20                  25                  30

Val Glu Asn Ile His Gly Ser Ala Ala Ile Ala Ser Ala Tyr Ser Arg
        35                  40                  45

Ala Tyr Glu Glu Thr Phe Thr Leu Thr Phe Val Thr Gly Arg Thr Val
    50                  55                  60

Gly Ile Gly Ala Tyr Leu Ala Arg Leu Gly Ile Arg Cys Ile Gln Arg
65                  70                  75                  80

Leu Asp Gln Pro Ile Ile Leu Thr Gly Phe Ser Ala Leu Asn Lys Leu
                85                  90                  95

Leu Gly Arg Glu Val Tyr Ser Ser His Met Gln Leu Gly Gly Pro Lys
            100                 105                 110

Ile Met Ala Thr Asn Gly Val Val His Leu Thr Val Pro Asp Asp Leu
        115                 120                 125

Glu Gly Val Ser Asn Ile Leu Arg Trp Leu Ser Tyr Val Pro Ala Asn
    130                 135                 140
```

```
Ile Gly Gly Pro Leu Pro Ile Thr Lys Pro Leu Asp Pro Pro Asp Arg
145                 150                 155                 160

Pro Val Ala Tyr Ile Pro Glu Asn Thr Cys Asp Pro Arg Ala Ala Ile
                165                 170                 175

Arg Gly Val Asp Asp Ser Gln Gly Lys Trp Leu Gly Gly Met Phe Asp
            180                 185                 190

Lys Asp Ser Phe Val Glu Thr Phe Glu Gly Trp Ala Lys Thr Val Val
        195                 200                 205

Thr Gly Arg Ala Lys Leu Gly Gly Ile Pro Val Gly Val Ile Ala Val
    210                 215                 220

Glu Thr Gln Thr Met Met Gln Leu Val Pro Ala Asp Pro Gly Gln Leu
225                 230                 235                 240

Asp Ser His Glu Arg Ser Val Pro Arg Ala Gly Gln Val Trp Phe Pro
                245                 250                 255

Asp Ser Ala Thr Lys Thr Ala Gln Ala Leu Leu Asp Phe Asn Arg Glu
            260                 265                 270

Gly Leu Pro Leu Phe Ile Leu Ala Asn Cys Arg Gly Phe Ser Gly Gly
        275                 280                 285

Gln Arg Asp Leu Phe Glu Gly Ile Leu Gln Ala Gly Ser Thr Ile Val
    290                 295                 300

Glu Asn Leu Arg Thr Tyr Asn Gln Pro Ala Phe Val Tyr Ile Pro Met
305                 310                 315                 320

Ala Gly Glu Leu Arg Gly Gly Ala Trp Val Val Val Asp Ser Lys Ile
                325                 330                 335

Asn Pro Asp Arg Ile Glu Cys Tyr Ala Glu Arg Thr Ala Lys Gly Asn
            340                 345                 350

Val Leu Glu Pro Gln Gly Leu Ile Glu Ile Lys Phe Arg Ser Glu Glu
        355                 360                 365

Leu Gln Asp Cys Met Gly Arg Leu Asp Pro Glu Leu Ile Asn Leu Lys
    370                 375                 380

Ala Lys Leu Gln Asp Val Lys His Gly Asn Gly Ser Leu Pro Asp Ile
385                 390                 395                 400

Glu Ser Leu Gln Lys Ser Ile Glu Ala Arg Thr Lys Gln Leu Leu Pro
                405                 410                 415

Leu Tyr Thr Gln Ile Ala Ile Arg Phe Ala Glu Leu His Asp Thr Ser
            420                 425                 430

Leu Arg Met Ala Ala Lys Gly Val Ile Lys Lys Val Val Asp Trp Glu
        435                 440                 445

Glu Ser Arg Ser Phe Phe Tyr Lys Arg Leu Arg Arg Arg Ile Ser Glu
    450                 455                 460

Asp Val Leu Ala Lys Glu Ile Arg His Ile Val Gly Asp Asn Phe Thr
465                 470                 475                 480

His Gln Ser Ala Met Glu Leu Ile Lys Glu Trp Tyr Leu Ala Ser Pro
                485                 490                 495

Ala Thr Thr Gly Ser Thr Gly Trp Asp Asp Asp Ala Phe Val Ala
            500                 505                 510

Trp Lys Asp Ser Pro Glu Asn Tyr Asn Gly Tyr Ile Gln Glu Leu Arg
        515                 520                 525

Ala Gln Lys Val Ser Gln Ser Leu Ser Asp Leu Thr Asp Ser Ser Ser
    530                 535                 540

Asp Leu Gln Ala Phe Ser Gln Gly
545                 550
```

HERBICIDE-RESISTANT GRAIN SORGHUM

CROSS-REFERENCE TO RELATED APPLICATIONS

This patent application claims the benefit of priority of U.S. Provisional Patent Application No. 62/943,663, filed Dec. 4, 2019, which is incorporated herein by reference in its entirety.

SEQUENCE LISTING

A Sequence Listing accompanies this application and is submitted as an ASCII text file of the sequence listing named "169946_00564_ST25.txt" which is 32.8 KB in size and was created on Oct. 14, 2020. The sequence listing is electronically submitted via EFS-Web with the application and is incorporated herein by reference in its entirety.

INTRODUCTION

Sorghum is the world's fifth most important cereal crop, after wheat, rice, maize, and barley. In addition to being an increasingly important food crop, sorghum is also an important animal feed and biofuel crop. This hardy crop is more tolerant to drought and excess soil moisture content than most cereals, and can be grown under varied soil and weather conditions. Consequently, sorghum is a critically important food crop in many of the driest regions of the world.

Weed control in grain sorghum (*Sorghum bicolor*) can be difficult due to limited available herbicides and the presence of herbicide-resistant weed species (Fromme et al. 2012). Moreover, control of johnsongrass and shattercane are especially difficult due to high genetic similarity with cultivated sorghum and a lack of selective herbicide options. Most postemergence (POST) herbicides labeled for grain sorghum are effective on broadleaf weed species, but have limited activity on annual grasses (Werle et al. 2016). Further, grass control options in grain sorghum is limited due to crop sensitivity and long rotation restrictions (Besancon et al. 2017).

The acetyl-CoA carboxylase (ACCase)-inhibiting herbicides are commonly used in various crops to selectively control annual and perennial grass species. There are three chemical families within the ACCase group, and each family has many unique active ingredients that provide excellent control of many grass weed species. However, grain sorghum is susceptible to ACCase-inhibitor herbicides, making the use of these herbicides almost impossible with conventional sorghum hybrids and open pollinated varieties.

Thus, the development of novel sorghum lines that are resistant to ACCase-inhibiting herbicides would increase the yields of this important crop plant in regions afflicted by grassy weeds, offering significant production and economic advantages.

SUMMARY

The present invention provides a novel sorghum cultivar designated '21534_ACCase-R', which is resistant to inhibition by fluazifop-p-butyl and other ACCase-inhibiting herbicides. The invention encompasses the seeds, plants, and plant parts of sorghum cultivar '21534_ACCase-R', as well as plants with essentially all of the physiological and morphological characteristics of '21534_ACCase-R'. Also disclosed is sorghum seed comprising a polynucleotide encoding the polypeptide of SEQ ID NO: 39, which confers resistance to damage by ACCase-inhibiting herbicides.

This invention also provides methods for producing a sorghum plant by planting seeds of cultivar '21534_ACCase-R', or seeds including a polynucleotide encoding the polypeptide of SEQ ID NO: 39 or by crossing sorghum '21534_ACCase-R' or seeds including a polynucleotide encoding the polypeptide of SEQ ID NO: 39 with itself or another sorghum line. Any plant breeding methods using sorghum variety '21534_ACCase-R' or seeds including a polynucleotide encoding the polypeptide of SEQ ID NO: 39 are part of this invention, including selfing, backcrosses, hybrid production, and crosses to populations. All plants and seeds produced using sorghum variety '21534_ACCase-R' or seeds including a polynucleotide encoding the polypeptide of SEQ ID NO: 39 as a parent are within the scope of this invention, including gene-converted plants of variety '21534_ACCase-R'. Methods for introducing a gene into variety '21534_ACCase-R', either through traditional breeding or transformation, are provided herein. Methods for introducing a polynucleotide encoding the polypeptide of SEQ ID NO: 39 into a sorghum plant are also provided.

In another aspect, the present invention provides regenerable cells for use in tissue culture of sorghum plant '21534_ACCase-R' or regenerable cells comprising a polynucleotide encoding a polypeptide of SEQ ID NO: 39, as well as sorghum plants regenerated from these tissue cultures.

DEFINITIONS

Figure 1:
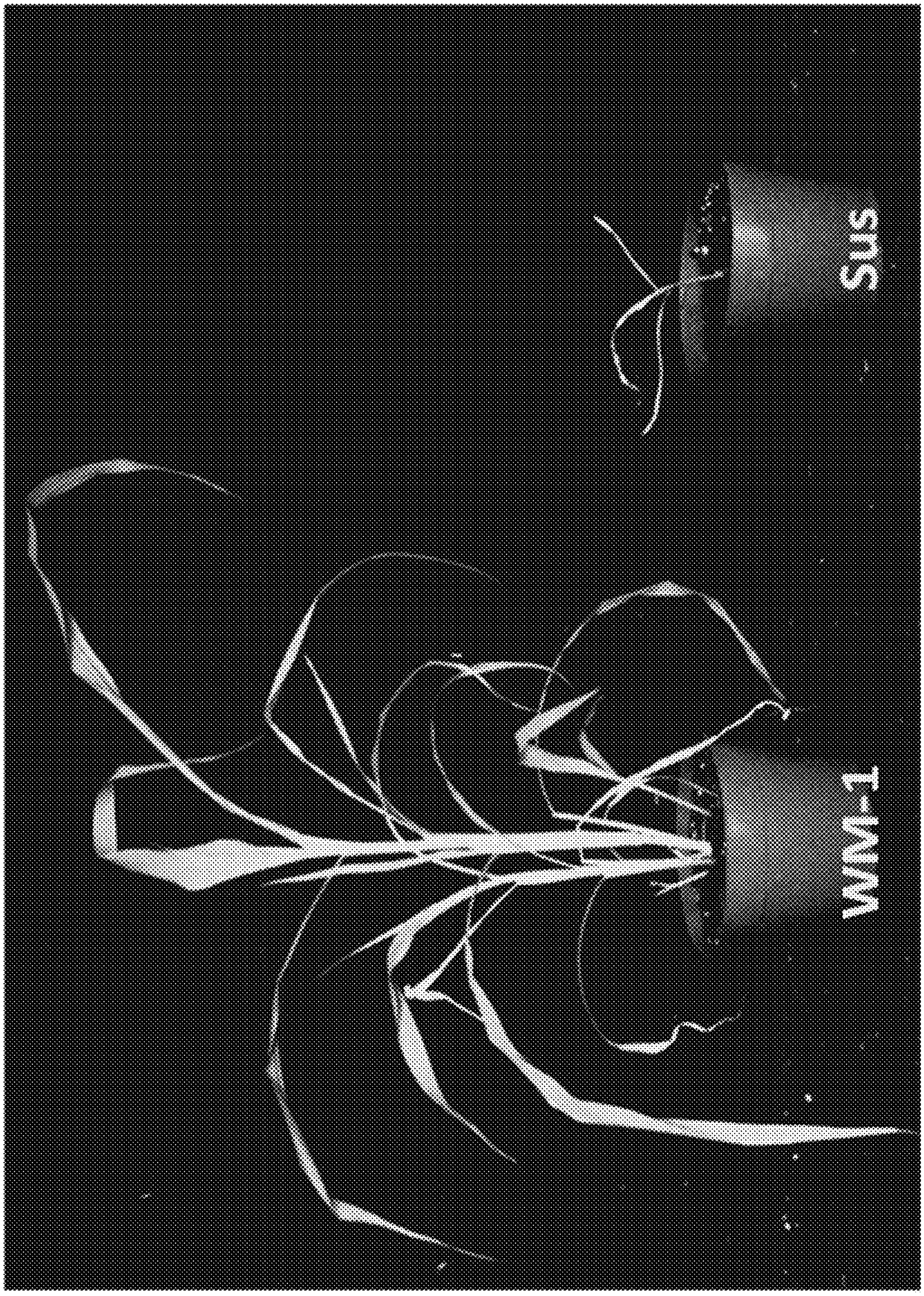
FIG. 1 demonstrates the tolerance of the fluazifop-resistant johnsongrass population (WM-1) to 4× the label rate (24 oz/A) applications compared to susceptible standard (Sus), at 35 days after treatment.

To provide a clear and consistent understanding of the specification and claims, the following definitions are provided:

Allele. One of two or more alternative forms of a gene, all of which relate to a single trait or characteristic. In a diploid cell or organism, two alleles of a given gene occupy corresponding loci on a pair of homologous chromosomes.

Backcrossing. A process in which a breeder repeatedly crosses hybrid progeny back to a parental line. For example, a first generation ($F_1$) hybrid may be crossed with one of the parental lines used to produce the $F_1$ hybrids.

Breeding. The genetic manipulation of living organisms.

Cell. As used herein, this term includes isolated cells, cells grown in tissue culture, and cells that comprise a plant or plant part.

Cultivar. Used interchangeably with “variety”. Refers to plants that are defined by the expression of the characteristics resulting from a given genotype or combination of genotypes, distinguished from any other plant grouping by the expression of at least one characteristic.

Diploid. A cell or organism having two complete sets of chromosomes.

Embryo. The plant embryo is the part of a seed or bud that contains the earliest forms of the new plant’s roots, stem and leaves.

Essentially all of the physiological and morphological characteristics. A plant having “essentially all the physiological and morphological characteristics” of the cultivar exhibits the characteristics of the cultivar with the exception of any characteristics derived from a converted gene.

F #. Denotes a filial generation, wherein the #is the generation number. For example, $F_1$ is the first filial generation.

Gene. Refers to a unit of inheritance corresponding to a distinct sequence of DNA or RNA nucleotides that form part of a chromosome. A gene may encode a polypeptide or a nucleic acid molecule that has a function in the cell or organism.

Herbicide resistant. Describes a plant that is tolerant or resistant to an herbicide at a level that would normally kill or inhibit the growth of a normal or wild-type sorghum plant.

Isogenic; also referred to as “gene-converted”. Describes a plant wherein essentially all of the desired morphological and physiological characteristics of a parental variety are maintained with the exception of a single trait that was transferred into the variety via backcrossing or genetic engineering.

Haploid. A cell or organism having a single set of unpaired chromosomes.

Hybrid. Refers to the offspring or progeny of genetically dissimilar plant parents or stock produced as the result of controlled cross-pollination as opposed to a non-hybrid seed produced as the result of natural pollination.

Pedigree. Refers to the lineage or genealogical descent of a plant.

Plant. As used herein, the term “plant” includes plant cells, plant protoplasts, and plant cell tissue cultures from which sorghum plants can be regenerated; plant calli, plant clumps and plant cells that are intact in plants; and plant parts including, without limitation, protoplasts, leaves, stems, roots, root tips, anthers, pistils, seed, grain, embryo, pollen, ovules, cotyledon, hypocotyl, pod, flower, shoot, tissue, petiole, cells, and meristematic cells.

Progeny. Includes an $F_1$ sorghum plant produced from the cross of two sorghum plants, as well as plants produced from subsequent generational crosses (e.g., $F_2$, $F_3$, $F_4$, $F_5$, $F_6$, $F_7$, $F_8$, $F_9$, and $F_{10}$) with the recurrent parental line.

Regeneration. Refers to the development of a plant from tissue culture.

Seeds. Includes seeds and plant propagules of all kinds including, but not limited to, true seeds, seed pieces, suckers, corms, bulbs, fruit, tubers, grains, cuttings, cut shoots and the like. However, in preferred embodiments, this term refers to true seeds.

Tetraploid. A cell or organism having four complete sets of chromosomes.

Trait. Refers to a genetically determined characteristic of an organism. For example, the present invention describes plants with fluazifop-resistance trait.

Transgenic. Describes an organism or cell that contains genetic material that has been artificially introduced.

Wild-type. When made in reference to a gene, “wild-type” refers to a gene common throughout a plant population and, thus, arbitrarily designated the “normal” or “wild-type”

form of the gene. Generally, "wild-type" is used to describe the functional form of a gene in contrast to a mutant and/or nonfunctional form.

DETAILED DESCRIPTION

The present invention provides a novel sorghum cultivar designated '21534_ACCase-R', which is resistant to inhibition by fluazifop-p-butyl and other ACCase-inhibiting herbicides. The invention encompasses both the seeds of this cultivar and plants grown from these seeds. The invention further encompasses any sorghum plant having essentially all of the physiological and morphological characteristics sorghum cultivar '21534_ACCase-R'.

Sorghum cultivar '21534_ACCase-R' was developed by transferring a fluazifop-p-butyl resistance trait identified in a population of johnsongrass into grain sorghum through rounds of crossing, selection, and identification of diploid progenies, as detailed in the Examples disclosed herein. Greenhouse experiments revealed that the resistance trait is conferred by a single gene with incomplete dominance. Subsequently, several rounds of backcrossing with elite sorghum lines and selection were carried out to improve the agronomic potential and eliminate unpreferable traits such as photoperiod sensitivity. The resulting diploid sorghum line shows tolerance to fluazifop and fenoxaprop at commercially acceptable levels to give rise to cultivar '21534_ACCase-R' provided herein. The single gene identified as responsible for providing resistance was identified and sequenced and is presented as SEQ ID NO: 39. Thus also provided herein are sorghum seeds comprising a polynucleotide encoding a polypeptide of SEQ ID NO: 39.

The inventors demonstrate the line tolerates over-the-top applications of fluazifop-p-butyl and fenoxaprop herbicides at rates which kill the wild-type plant. Thus, this invention will allow for effective control of grass weeds in sorghum using post-emergence applications of fluazifop or fenoxaprop.

Herbicide Resistance

Sorghum cultivar '21534_ACCase-R' and sorghum plants comprising a polynucleotide encoding the polypeptide of SEQ ID NO: 39 are resistant to fluazifop-p-butyl (chemical formula R-2-[4-[[5-(trifluoromethyl)-2-pyridinyl]oxy]phenoxy] propanate). This herbicide, also referred to as "fluazifop", belongs to the aryloxyphenoxy-propionate herbicide family and is available under several trade names, including Fusilade®, Horizon 2000®, Ornamec®, Fusion®, and Tornado®. Fluazifop-p-butyl is a postemergence herbicide. It is absorbed rapidly through leaf surfaces and quickly hydrolyzes to fluazifop acid. The acid is transported primarily in the phloem and accumulates in the meristems where it disrupts the synthesis of lipids in susceptible species (Urano 1982; Erlingson 1988). Specifically, fluazifop-p-butyl inhibits acetyl CoA carboxylase (ACCase), an enzyme that catalyzes the carboxylation of acetyl-CoA to produce malonyl-CoA in an early step of fatty acid synthesis. Lipids are important components of cellular membranes, and when they cannot be produced in sufficient quantities, cell membrane integrity fails, especially in regions of active growth such as meristems. Both annual and perennial grasses can be controlled by fluazifop-based herbicides, including bromes (*Bromus* spp.), quackgrass (*Elytrigia repens*), johnsongrass (*Sorghum halepense*), and panic or witch-grasses (*Panicum* spp.). Thus, the sorghum and sorghum seeds provided with the present invention may be used with these herbicides to control monocot weeds that grow in the presence of these crops.

In addition to fluazifop-p-butyl and fenoxaprop, the inventors envision that the seeds and plants disclosed herein may be resistant to other ACCase inhibiting herbicides, including others from the aryloxyphenoxypropionate (FOP) herbicide family, such as clodinafop-propargyl, cyhalofop-butyl, diclofop-methyl, fenoxaprop-p-ethyl, haloxyfop-ethoxyethyl, haloxyfop-etotyl, haloxyfop-R-methyl, propaquizafop, quizalofop-p-ethyl, pinoxaden, diclofop-methyl, and quizalo-P-refuryl compounds. Thus, this invention encompasses the use of any ACCase-inhibiting herbicide, as well as the use of combinations of such compounds. In preferred embodiments, the herbicide used with the present invention is fluazifop-p-butyl, fenoxaprop-p-ethyl, cyhalofop-butyl, quizalofop-p-ethyl, clodinafop-propargyl, pinoxaden, diclofop-methyl, or a combination thereof.

As is demonstrated in the Examples, herbicide resistance may be measured as percent crop injury following treatment with an herbicide. Crop injury can be measured by any of the various methods known in the art. For example, crop injury can be determined as a percentage as compared to untreated plants following a standard procedure wherein crop injury is visually assessed by one skilled in the art. A "commercially acceptable rate of crop injury" for the present invention likewise varies with the crop plant species. Typically, a commercially acceptable rate of crop injury is defined as less than about 25%, 20%, 18%, 16%, 15%, 13%, 12%, 11%, 10% or even less than about 5% injury. In the Examples the inventors demonstrate that sorghum cultivar '21534_ACCase-R' (or plants expressing the polypeptide of SEQ ID NO: 39) exhibits crop injury at a commercially acceptable rate after treatment with specific ACCase inhibiting herbicides. Specifically, in Example 3, this cultivar showed commercially acceptable tolerance to fluazifop (2% injury) fenoxaprop-p-ethyl (3% injury), cyhalofop-butyl (5% injury), quizalofop-p-ethyl (5% injury), clodinafop-propargyl (7% injury), pinoxaden (9% injury), diclofop-methyl (4% injury), and a combination of fluazifop and fenoxaprop (12% injury) at 2 weeks after treatment at a 1× rate of herbicide at the 2- to 3-leaf stage (see Table 4).

The herbicide may be applied at pre-emergence, post-emergence, pre-planting or at planting to control weeds in areas surrounding the sorghum plants described herein. In some embodiments, herbicide application allows for more than 70%, 80%, 85%, 90%, or 95% control of seedling and rhizomatous johnsongrass. (See Table 5).

The preferred method of herbicide application will depend on the herbicide of choice. In embodiments in which fluazifop-p-butyl is utilized, the application is preferably post-emergence. The herbicide can be applied in the media, irrigation water, or hydroponic solutions used to propagate plants, or can be applied directly to the foliage of plants being grown in soil or in other media in a field, greenhouse, or plant growth chamber. Treated plants may range in age from the presence of a single leaf collar to physiological maturity, which is identified by the presence of a black layer at the base of the mature caryopsis. An herbicide can be used by itself or as part of an herbicide formulation that contains other additives. Customary formulations include, for example solutions, emulsions, suspensions, dusts, powders, pastes and granules. The use form of an herbicide depends on the particular intended purpose; in each case, it should ensure a fine and even distribution of the compound according to the invention. Additives that may be found in an herbicide formulation include other herbicides, detergents, adjuvants, spreading agents, sticking agents, stabilizing agents, or the like. The herbicide formulation can be a wet or dry preparation and can include, but is not limited to, flowable powders, emulsifiable concentrates and liquid concentrates. Such formulations are prepared in a known manner, for example by extending the active compound with auxiliaries suitable for the formulation of agrochemicals, such as solvents and/or carriers, emulsifiers, surfactants and dispersants, preservatives, antifoaming agents, anti-freezing agents, and also optionally colorants and/or binders and/or gelling agents.

With the present invention, the preferred amount or concentration of the herbicide is an “effective amount” or “effective concentration,” i.e., an amount or concentration that is sufficient to kill or inhibit the growth of a similar, wild-type sorghum plant, sorghum plant tissue, sorghum plant cell, sorghum seed or any of the weed species noted above, but that said amount does not kill or inhibit as severely the growth of the herbicide-resistant plants, plant tissues, plant cells, and seeds of the present invention. Typically, the effective amount of an herbicide is an amount that is routinely used in agricultural production systems to kill weeds of interest. Label rates of herbicides include, for example, 0.125 pounds of active ingredient per acre (lb ai/A) for fluazifop, 0.077 lb ai/A for fenoxaprop, 0.041 lb ai/A for quizalofop, and 0.12 lb ai/A for clethodim. In some embodiments, the sorghum plants are treated with fluazifop at a rate ranging from about 0.1 to about 0.2 lb ai/A. In other embodiments, the sorghum plants are treated with fenoxaprop at a rate ranging from about 0.05 to about 0.1 lb ai/A. In other embodiments, the sorghum plants are treated with quizalofop at a rate ranging from about 0.02 to about 0.06 lb ai/A. In other embodiments, the sorghum plants are treated with clethodim at a rate ranging from about 0.08 to about 0.2 lb ai/A. Such amounts are known to those of ordinary skill in the art, and may be adjusted according to the particular crops, weeds, and environmental conditions at hand.

Sorghum cultivar ‘21534_ACCase-R’ was also selected for photoperiod insensitivity. “Photoperiod sensitivity” refers to the sensitivity of the flowering time of plants relative to daylength in which it is grown. Some plants do not flower until they are exposed to daylengths that are less than a specific photoperiod (short day plants) or greater than a specific photoperiod (long day plants). Sorghum is a facultative short-day plant for which long days delay flowering while short days accelerate reproductive growth. The degree of photoperiod sensitivity in sorghum refers to the length of daylight required to induce flowering. A highly photoperiod sensitive sorghum requires photoperiods of about 12 hours before reproductive growth is initiated whereas plants with moderate photoperiod sensitivity require daylengths less than about 14 hours to induce flowering. True photoperiod insensitive genotypes are not influenced by daylength in any situation, and will flower in any length of daylight (assuming that seasonal temperatures allow for growth).

Different sorghum cultivars vary in their degree of photoperiod sensitivity. Sorghum inbreds have been identified with photoperiod sensitivity ranging from ~10.5 to ~14 hours while others are insensitive to photoperiod. To maximize yield, it is important to tailor the plants’ life cycle to the environments in which they are grown. Thus, the use of “photoperiod insensitive” or “early flowering plants” is advantageous in regions with short growing seasons.

Methods

This present invention provides methods for producing sorghum plants. In some embodiments, these methods involve planting a plurality of sorghum seeds provided herein under conditions favorable for the growth of sorghum plants. The sorghum seeds may be of variety ‘21534_ACCase-R’ or may be plants comprising a polynucleotide encoding the polypeptide of SEQ ID NO: 39.

As used herein, the term plant includes plant cells, plant protoplasts, plant cell tissue cultures from which sorghum plants can be regenerated, plant calli, plant clumps and plant cells that are intact in plants or parts of plants, such as embryos, pollen, ovules, flowers, glumes, panicles, leaves, stems, roots, root tips, anthers, pistils, and the like.

The present invention also provides methods for producing a sorghum seed or plant by crossing a first parent sorghum plant with a second parent sorghum plant, wherein either the first or second parent sorghum plant is of the line ‘21534_ACCase-R’ or comprises a polynucleotide encoding the polypeptide of SEQ ID NO: 39, such that the plant is resistant to ACCase inhibitor herbicides. In some embodiments, a breeding cross is made to introduce new genetics into the ‘21534_ACCase-R’ progeny or progeny comprising the polypeptide of SEQ ID NO: 39 (as opposed to a self or a sib cross, made to select among existing genetic alleles). In these embodiments, a population of hybrid sorghum plants will be produced that, on average, derive 50% of their alleles from cultivar ‘21534_ACCase-R’ and will be selected to include the polynucleotide encoding the polypeptide of SEQ ID NO: 39. The resulting first generation ($F_1$) hybrid sorghum seeds may be harvested and used to grow plants that express a subset of characteristics from ‘21534_ACCase-R’. Alternatively, a plant of this population may be selected and repeatedly selfed or sibbed with a sorghum cultivar resulting from successive filial generations. In other embodiments, both the first and second parent sorghum plants can come from the sorghum cultivar ‘21534_ACCase-R’. However, advantageously, the sorghum cultivar is used in crosses with other, different, sorghum cultivars to produce $F_1$ sorghum seeds and plants with superior characteristics. In some embodiments, the sorghum cultivar ‘21534_ACCase-R’ is crossed with a second sorghum plant that is transgenic. See the section below titled “Breeding Methods” for a detailed description of breeding techniques that may utilized with the present invention.

In some embodiments, a ‘21534_ACCase-R’ progeny plant is selected that has molecular markers, morphological characteristics, and/or physiological characteristics in common with ‘21534_ACCase-R’. Techniques such as RFLP-enhanced selection, genetic marker enhanced selection (e.g., SSR markers), and the making of double haploids may be utilized to identify progeny that share particular traits with ‘21534_ACCase-R’.

Further, this invention provides methods for introducing a desired trait into sorghum cultivar ‘21534_ACCase-R’. This may be accomplished using traditional breeding methods, such as backcrossing. Here, sorghum cultivar ‘21534_ACCase-R’ is crossed with a second sorghum line expressing the desired trait and progeny with both the desired trait and characteristics of ‘21534_ACCase-R’ are selected and crossed. These steps are repeated until plants with both the desired trait and essentially all the physiological and morphological characteristics of ‘21534_ACCase-R’ have been produced.

Alternatively, the desired trait may be introduced by transforming the sorghum cultivar with a transgene. The transgene may confer at least one trait selected from the following: herbicide resistance; insect resistance; resistance to bacterial, fungal, or viral disease; modified fatty acid metabolism; modified carbohydrate metabolism; and male sterility. See the section below titled “Transformation Methods” for a detailed description of transformation techniques that may utilized with the present invention. The transgenic cultivar produced by these methods may be crossed with another cultivar to produce a new transgenic cultivar. Alternatively, the transgene incorporated by these methods could be moved into another cultivar using traditional backcrossing techniques.

Optionally, any of the disclosed methods may further comprise additional steps involving producing sorghum seed from the resulting sorghum plants and/or planting the sorghum seed.

The present invention encompasses all plants, or parts thereof, produced by the methods described herein, as well as the seeds produced by these plants. Further, any plants derived from sorghum cultivar ‘21534_ACCase-R’ or produced from a cross using cultivar ‘21534_ACCase-R’ or comprising SEQ ID NO: 39 are provided. This includes genetic variants, created either through traditional breeding methods or through transformation, as well as plants produced in a male-sterile form. Notably, this includes gene-converted plants developed by backcrossing. Any of the seeds, plants, or plant parts provided may be utilized for human food, livestock feed, and as a raw material in industry.

The present invention also encompasses progeny of sorghum cultivar ‘21534_ACCase-R’ comprising a combination of at least two ‘21534_ACCase-R’ traits associated with sorghum cultivar ‘21534_ACCase-R’, wherein the progeny sorghum plant is not significantly different from ‘21534_ACCase-R’ for said traits, as determined at the 5% significance level when grown in the same environment. One of skill in the art knows how to compare a trait between two plant varieties to determine if there is a significant difference between them (Fehr and Walt, Principles of Cultivar Development, pp. 261-286 (1987)). Molecular markers or mean trait values may be used to identify a plant as progeny of ‘21534_ACCase-R’. Alternatively, progeny may be identified through their filial relationship with sorghum cultivar ‘21534_ACCase-R’ (e.g., as being within a certain number of breeding crosses of sorghum cultivar ‘21534_ACCase-R’). For example, progeny produced by the methods described herein may be within 1, 2, 3, 4, or 5 breeding crosses of sorghum cultivar ‘21534_ACCase-R’.

Tissue Culture/Embryo Rescue

The present invention provides tissue cultures of regenerable cells or protoplasts produced from sorghum cultivar ‘21534_ACCase-R’. As is well known in the art, tissue culture of sorghum can be used for the in vitro regeneration of a sorghum plant. Tissues such as cells and protoplasts may be used to produce plants having the physiological and morphological characteristics of sorghum variety ‘21534_ACCase-R’. Further, embryo rescue may be performed to allow plants to be produced following cross-pollination of distantly related species. The sorghum plants generated by these methods are also encompassed by the present invention.

As used herein, the term “tissue culture” describes a composition comprising isolated cells or a collection of such cells organized into parts of a plant. Exemplary tissues for culture include protoplasts, calli, plant clumps, and plant cells that can be grown in culture, or parts of plants, such as embryos, pollen, flowers, seeds, pods, leaves, stems, roots, root tips, and anthers. Culture of various sorghum tissues and regeneration of plants therefrom is well known in the art.

Breeding Methods

The goal of sorghum breeding is to develop new, superior sorghum cultivars and hybrids.

A superior cultivar is produced when a new combination of desirable traits is formed within a single plant variety. Desirable traits may include higher seed yield, resistance to diseases and insects, better stems and roots, tolerance to low temperatures, and better agronomic characteristics or grain quality. Thus, breeding methods may be used to combine additional desirable traits with the fluazifop-resistance of sorghum cultivar ‘21534_ACCase-R’.

The breeding methods used with the present invention may involve a single-seed descent procedure, in which one seed per plant is harvested and used to plant the next generation. Alternatively, the methods may utilize a multiple-seed procedure, in which one or more seeds harvested from each plant in a population is threshed together to form a bulk which is used to plant the next generation.

Use of sorghum cultivar ‘21534_ACCase-R’ in any plant breeding method is encompassed by the present invention. The choice of a breeding or selection method will depend on several factors, including the mode of plant reproduction, the heritability of the trait(s) being improved, and the type of cultivar used commercially (e.g., $F_1$ hybrid cultivar, pureline cultivar). Popular selection methods include pedigree selection, modified pedigree selection, mass selection, recurrent selection, backcrossing, or a combination thereof.

Sorghum plants are self-pollinating, but they can also be bred by cross-pollination. A plant is considered “self-pollinating” if pollen from one flower can be transmitted to the same or another flower, whereas plants are considered “cross-pollinated” if the pollen has to come from a flower on a different plant in order for pollination to occur. The development of sorghum hybrids requires use of the cytoplasmic male sterility-fertility restorer system. In this system, pollinator parents (i.e., lines with fertility restoring genes) are crossed to seed parent inbreds, which are typically created to be cytoplasmically male sterile, thereby requiring cross-pollination. Thus, in these crosses, seed is provided by the seed-parent lines while pollen is provided by the pollinator-parent lines to produce a single cross hybrid.

Pedigree selection is commonly used for the improvement of self-pollinating crops. Two parents are crossed to produce an $F_1$ population. An $F_2$ population is produced by selfing one or several $F_1$'s. Selection of the best individuals may begin in the $F_2$ population; then, beginning in the $F_3$ generation, the best individuals in the best families are selected. Replicative testing of families can begin in the $F_4$ generation to make selection of traits with low heritability more effective. At an advanced stage of inbreeding (e.g., $F_6$ or $F_7$), the best lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population, which is often subjected to additional cycles of selection.

Backcrossing is commonly used to transfer genes for highly heritable traits into a desirable homozygous cultivar or inbred line. The term “backcrossing” refers to the repeated crossing of hybrid progeny back to one of the parental plants, referred to as the recurrent parent. The plant that serves as the source of the transferred trait is called the donor parent. After the initial cross, individuals possessing the transferred trait are selected and repeatedly crossed to the recurrent parent. The resulting plant is expected to have the attributes of the recurrent parent along with the trait transferred from the donor parent.

Transformation Methods

As is noted above, the present invention provides plants and seeds of sorghum cultivar '21534_ACCase-R' in which herbicide resistance has been transferred. While such traits may be selected for using traditional breeding methods, they may also be introduced as transgenes. "Transgenes" include both foreign genes and additional or modified versions of native genes. Plants can be genetically engineered to have a wide variety of traits of agronomic interest including, without limitation, male sterility, waxy starch, herbicide resistance, resistance for bacterial, fungal, or viral disease, insect resistance, male fertility, enhanced nutritional quality, industrial usage, yield stability, and yield enhancement. Many examples of genes that confer such traits have been described in the literature and are well known in the art. For example, the transgene may confer resistance to an additional herbicide selected from the group consisting of: glyphosate, sulfonylurea, imidazolinone, dicamba, glufosinate, phenoxy proprionic acid, L-phosphinothricin, cyclohexone, cyclohexanedione, triazine, 2,4-Dichlorophenoxyacetic acid, hydroxyphenyl-pyruvate dioxygenase (HPPD) inhibitors, and benzonitrile.

Transgenes are typically introduced in the form of an expression vector. As used herein, an "expression vector" is DNA comprising a gene operatively linked to a regulatory element (e.g., a promoter). The expression vector may contain one or more such gene/regulatory element combinations. The expression vector may also include additional sequences, such as a signal sequence or a tag, that modify the protein produced by the transgene. The vector may be a plasmid, and can be used alone or in combination with other plasmids.

Expression vectors include at least one genetic marker operably linked to a regulatory element (e.g., a promoter) that allows transformed cells containing the vector to be recovered by selection. In some embodiments, negative selection (i.e., inhibiting growth of cells that do not contain the selectable marker gene) it utilized. Negative selection markers include, for example, genes that result in detoxification of a chemical agent (e.g., an antibiotic or an herbicide) and genes that result in insensitivity to an inhibitor. Exemplary negative selection genes include neomycin phosphotransferase II (nptII), hygromycin phosphotransferase, gentamycin acetyl transferase, streptomycin phosphotransferase, and aminoglycoside-3'-adenyl transferase. In other embodiments, positive selection (i.e., screening for the product encoded by a reporter gene) is utilized. Exemplary reporter genes include β-glucuronidase, β-galactosidase, luciferase, chloramphenicol acetyltransferase, and Green Fluorescent Protein (GFP).

Transgene expression is typically driven by operably linking the transgene to a promoter within the expression vector. However, other regulatory elements may also be used to drive expression, either alone or in combination with a promoter. As used herein, a "promoter" is a region of DNA upstream of a transcription start site that is involved in recognition and binding of RNA polymerase for transcription initiation. Any class of promoter may be selected to drive the expression of a transgene. For example, the promoter may be "tissue-specific", "cell type-specific", "inducible", or "constitutive". Those of skill in the art know how to select a suitable promoter based the particular circumstances and genetic engineering goals.

Methods for producing transgenic plants are well known in the art. General descriptions of plant expression vectors, reporter genes, and transformation protocols can be found in Gruber, et al., "Vectors for Plant Transformation", in *Methods in Plant Molecular Biology & Biotechnology* in Glich, et al., (Eds. pp. 89-119, CRC Press, 1993). General methods of culturing plant tissues are provided for example by Maki, et al., "Procedures for Introducing Foreign DNA into Plants" in *Methods in Plant Molecular Biology & Biotechnology*, Glich, et al., (Eds. pp. 67-88 CRC Press, 1993); and by Phillips, et al., "Cell-Tissue Culture and In-Vitro Manipulation" in *Corn & Corn Improvement,* 3rd Edition; Sprague, et al., (Eds. pp. 345-387 American Society of Agronomy Inc., 1988). Methods of introducing expression vectors into plant tissue include direct gene transfer methods, such as microprojectile-mediated delivery, DNA injection, and electroporation, as well as the direct infection or co-cultivation of plant cells with *Agrobacterium tumefaciens*, described for example by Horsch et al., *Science,* 227:1229 (1985). Descriptions of *Agrobacterium* vector systems and methods for *Agrobacterium*-mediated gene transfer are provided by Gruber, et al., supra.

EXAMPLES

Example 1: Development of a Fluazifop-Resistant Grain Sorghum Breeding Line

The following Example describes the development of a novel grain sorghum breeding line that has tolerance to the ACCase-inhibiting herbicide fluazifop, i.e., the active ingredient in the herbicide Fusilade®.

Transfer of a Fluazifop-Resistance Trait into Sorghum

A fluazifop-resistant johnsongrass population collected near West Memphis, Ark. (referred to as "WM") was utilized for transferring the resistance trait to grain sorghum. Fluazifop was applied at a 4× field rate (1×=6 oz/A of Fusilade) to the johnsongrass, and ten highly surviving individuals were selected from the $F_2$ generation of the WM population and were transferred to Texas. One of the three most tolerant individuals (WM-1) was selected for subsequent use. Dose-response assays revealed that the WM population exhibited >30-fold resistance to the fluazifop-p-butyl herbicide Fusilade® compared to a susceptible standard (FIG. 1). A target-site mutation in the ACCase gene (Tryptophan2027>Cysteine) was found to be responsible for the resistance in the johnsongrass population.

Initial crosses were made between WM-1 and a line of male sterile (MS) sorghum (X Tx3361iap), using the MS sorghum line as the female parent. The seeds obtained from this cross were germinated in greenhouse flats and the seedlings were sprayed at 2× (12 oz/A) the label rate of Fusilade.

Figure 2:
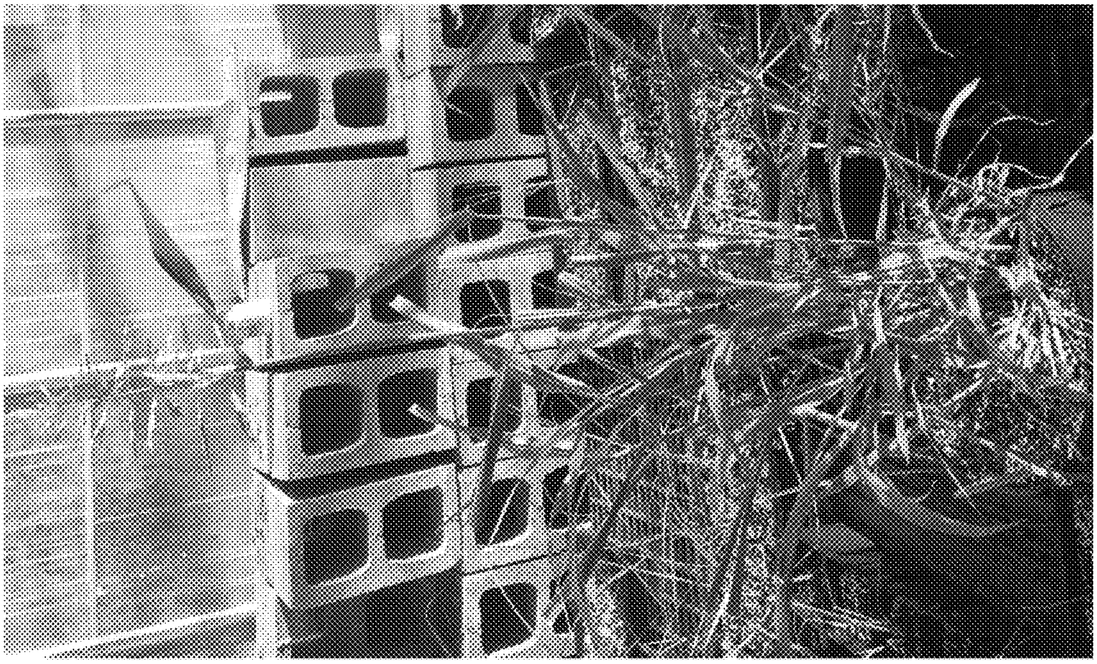
FIG. 2 shows the phenotype of a triploid $BC_1F_1$ progeny with tolerance to fluazifop.

The most tolerant plant was selected from the resulting $F_1$ progeny. Flow cytometry analysis revealed that this plant was a tetraploid, as were other survivors of the screening. This plant was also male sterile, and was subsequently used for backcrossing with *S. bicolor* pollen (Tx2783). A triploid embryo was rescued from the panicle of the resulting $F_1$ progeny and nurtured in an agar media standardized for this purpose. The triploid seedling was transferred to a pot and established in the greenhouse (FIG. 2).

Backcrossing and Identification of Diploid Progeny

Figure 3:
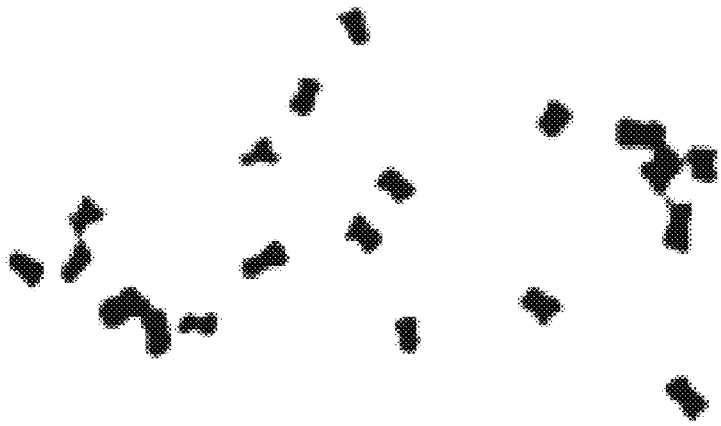
FIG. 3 shows a confirmation of the presence of 20 chromosomes in the diploid fluazifop-resistant *S. bicolor.*

Multiple backcrosses were made using the triploid plant ($BC_1F_1$) as the female parent and Tx2783 as the male parent. The $BC_2F_1$ progenies were sprayed with a 1× (6 oz/A) rate of fluazifop and flow cytometry was conducted to identify potential diploid individuals. Three selected individuals, identified as diploids in the flow cytometry analysis, were karyotyped to confirm chromosome numbers. An individual with 20-chromosomes was selected for subsequent breeding (FIG. 3). The majority of the flowers in this plant were male-fertile.

Figure 4:
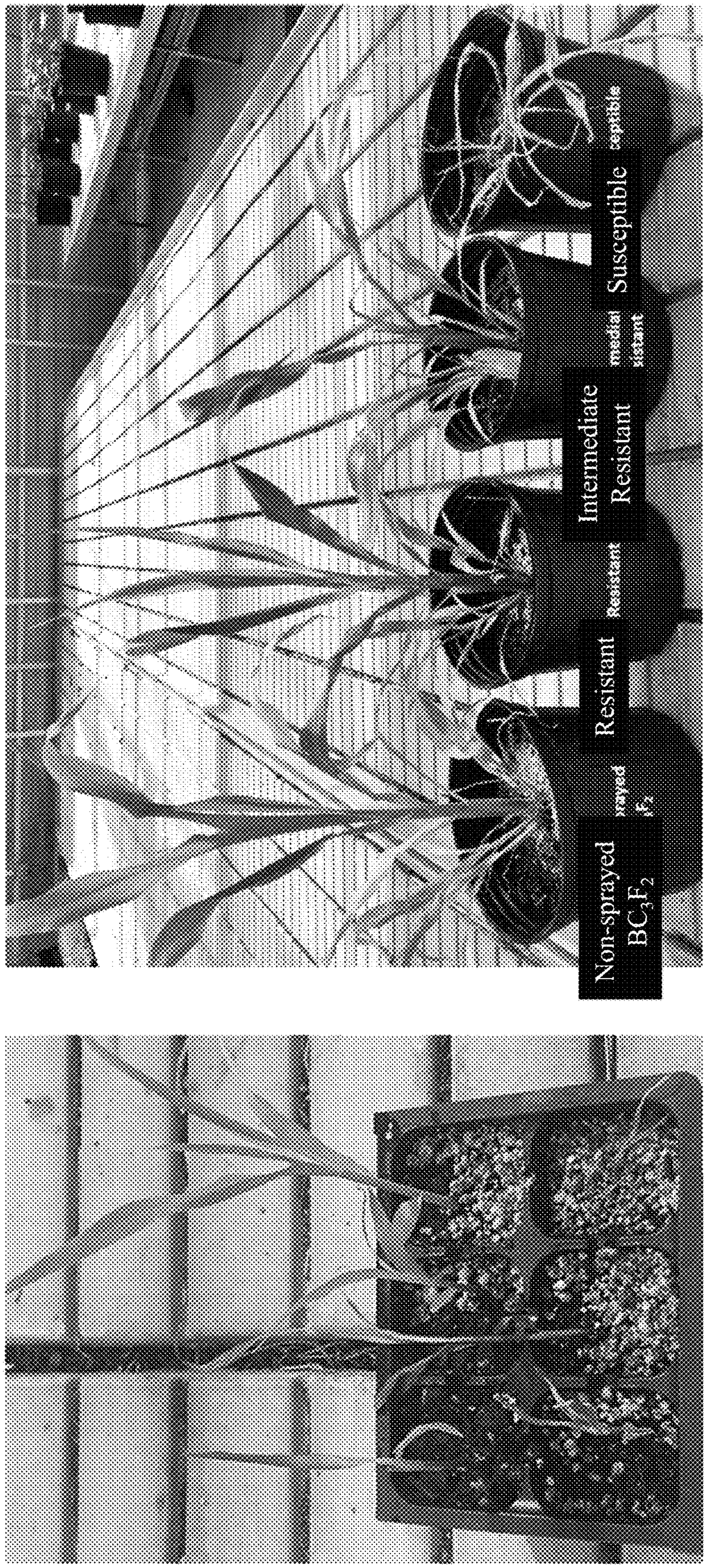
FIG. 4 shows the segregation of the tolerance trait in sorghum when herbicide was applied at an early seedling stage (left) or at 6" growth stage (right).

Following the identification of the 20-chromosome individual, multiple backcrosses were made using male sterile sorghum line Tx623 (female). The progenies were tested for their tolerance to the herbicide at two growth stages in the greenhouse, at early seedling stage and at 6" growth stage. In both evaluations, the seedlings showed a clear segregation of the resistance trait, conforming to Mendelian inheritance (FIG. 4). Results indicated that the fluazifop resistance in the developed *S. bicolor* lines is conferred by a single, incompletely dominant gene.

Selection for Improved Agronomic Potential

Figure 5B:
FIG. 5B shows the segregation of resistance in the population.
Figure 5A:
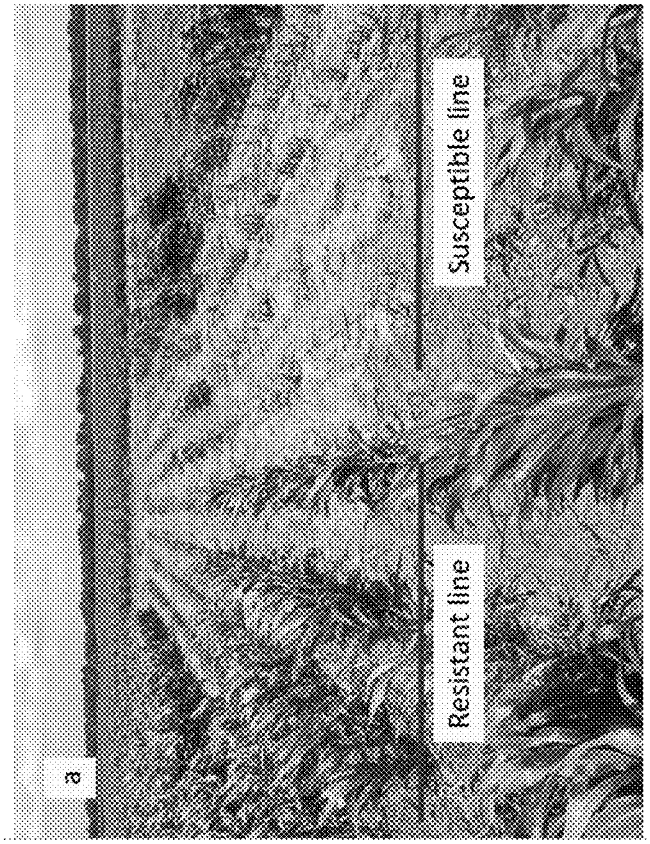
FIG. 5A shows the tolerance of the fluazifop-resistant grain sorghum line, compared to a susceptible standard, in a field test conducted in College Station, Tex.

A field experiment was conducted during in the summer in College Station, Tex. to confirm field-level expression of the resistance trait. Results showed a clear tolerance at a 6 oz/A rate of fluazifop (FIG. 5A), but the trait was still segregating (FIG. 5B). Moreover, photoperiod sensitivity was evident.

Figure 6:
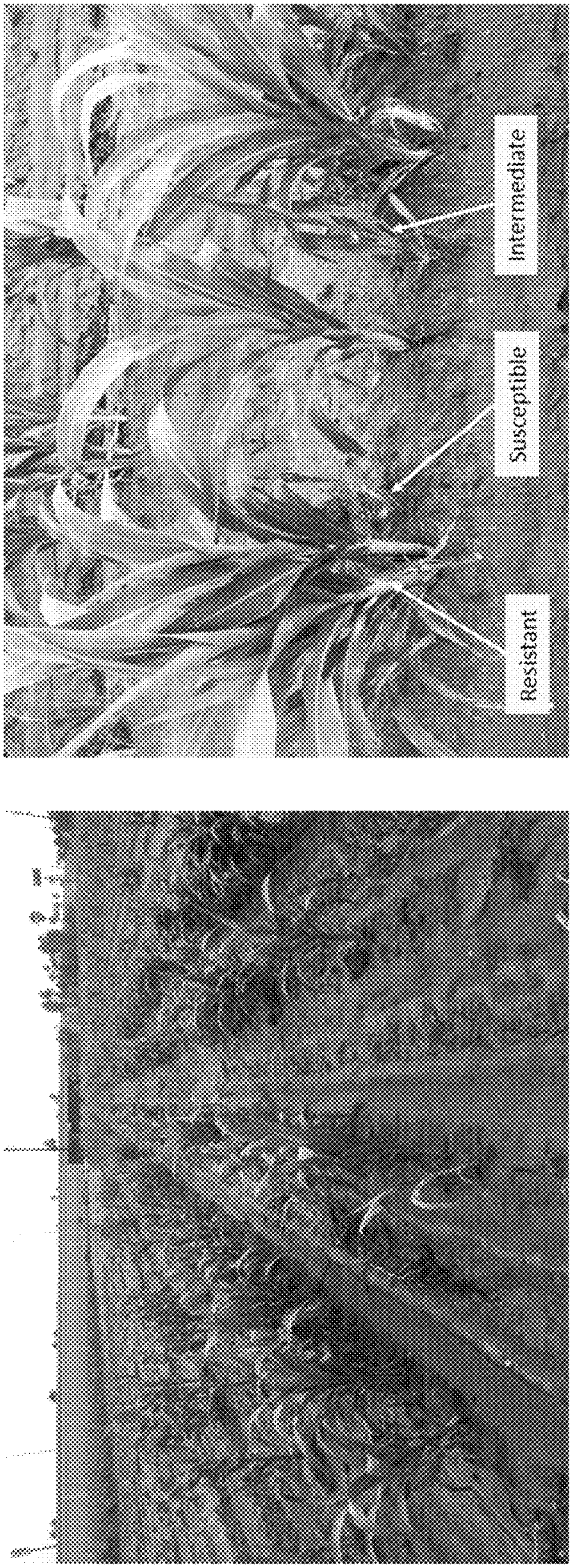
FIG. 6 shows a field view of the selections conducted in Weslaco, Tex. (left); the trait was still segregating for resistance, showing highly tolerant, intermediate and susceptible individuals (right).

To eliminate photoperiod sensitivity from the population, the early flowering individuals in the above field evaluation were bagged and seeds were harvested at maturity. The seeds were then planted in Weslaco, Tex. for another cycle of selection. The seedlings were sprayed with 6 oz/A fluazifop. The survivors (FIG. 6) were observed and early flowering individuals were bagged. This evaluation also helped select individuals with the highest fluazifop tolerance (i.e., those that likely had two copies of the resistance-conferring gene). The seed harvested from Weslaco were sent to winter nursery in Peurto Rico for selfing and seed increase.

Figure 7:
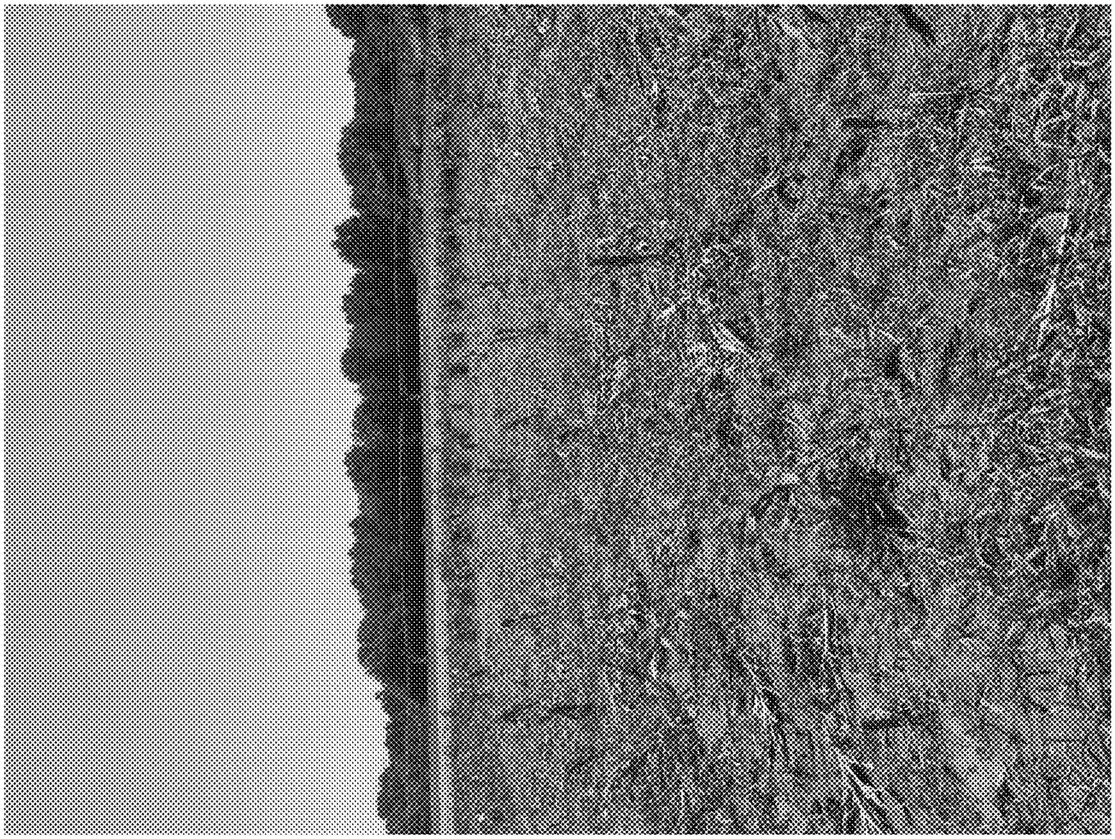
FIG. 7 shows the evaluations conducted in Fayetteville, Ark. to evaluate sorghum tolerance to fluazifop and selection for tolerant individuals.

Selections were carried out in College Station, Tex. in the summer using seed harvested from Puerto Rico. Parallel evaluations were also conducted in Fayetteville, Ark. during mid-summer to early fall to verify crop tolerance (FIG. 7). Surviving individuals were selected and seeds were harvested for subsequent testing.

Figure 8:
FIG. 8 shows a field view of the fluazifop-resistant sorghum line in College Station, Tex.

Field selections were continued in College Station, Tex. and Fayetteville, Ark. These selections have produced a line showing commercially acceptable tolerance to field applications of fluazifop. Notably, the resistance trait is fixed in this population, without any segregation (FIG. 8), and photoperiod sensitivity was successfully eliminated.

Example 2: Characterization of the Fluazifop-Resistant Grain Sorghum Breeding Line Under Greenhouse Conditions The following Example describes experiments that were performed to evaluate the grain sorghum line disclosed herein under greenhouse conditions. Specifically, the fluazifop-resistant sorghum was tested to (1) determine its response to various doses of fluazifop at various growth stages, (2) assess whether it has cross-resistance to other ACCase-inhibiting herbicides, and (3) identity the target-site mutations that confer its fluazifop resistance.

Plant Material

The cultivar DKS 45-23 (Dekalb, Bayer, USA) was used as an ACCase-susceptible grain sorghum standard. Selection 18PR-308 was utilized as the ACCase-resistant grain sorghum line in this experiment.

Herbicide Dose-Response Assays

Experimental setup: Herbicide dose-response assays were conducted in a greenhouse located in Fayetteville, Ark. in 2019. Approximately 3 seeds were placed in 10 cm-diameter pots filled with a mixture of 50% of potting soil (Pro-Mix M®, Premier Horticulture Inc., Quakertown, Pa. 18951) and 50% sieved silt loam soil (pH of 6.6 and 2.4% organic matter). The soil was collected in Fayetteville. At emergence, seedlings were thinned to achieve a density of 1 seedling in each pot. Plants were grown under a 35/25 C day/night temperature regime and a 16-hour photoperiod supplemented with light emitting diode lighting, and the pots were watered daily, multiple times if needed.

Herbicides and application: Two experiments were conducted. In the first experiment, a dose-response assay was conducted to determine the level of tolerance of the 18PR-308 sorghum line to fluazifop (Table 1) at three different growth stages (2-leaf, 3- to 4-leaf, and 5- to 6-leaf). The dose-response assay included seven doses for the fluazifop-resistant grain sorghum (1×, 2×, 4×, 8×, 16×, 32× and 64×) and six doses for the susceptible standard (1/32×, 1/16×, 1/8×, 1/4×, 1/2× and 1×). The field rate (1×) used was 105 g ai $ha^{-1}$ for fluazifop, and all treatments included a crop oil concentrate (COC) at 1% v/v. All treatments were applied using a spray chamber equipped with 1100067 nozzles calibrated to deliver 187 L $ha^{-1}$ at 1.6 km $h^{-1}$. Data were regressed by herbicide and genotype with a nonlinear 3P logistic curve using "drc" package in R (version 3.5.3).

TABLE 1

Rates used to evaluate grain sorghum sensitivity to fluazifop.

| | Rate designation | Rate (g ai $ha^{-1}$) |
|---|---|---|
| DKS 45-23 | 0x | 0 |
| (Susceptible) | 0.03125x | 3 |
| | 0.0625x | 7 |
| | 0.125x | 13 |
| | 0.25x | 26 |
| | 0.5x | 53 |
| | 1x | 105 |
| 18PR-308 | 0x | 0 |
| (Resistant) | 1x | 105 |
| | 2x | 211 |
| | 4x | 422 |
| | 8x | 843 |
| | 16x | 1686 |
| | 32x | 3373 |
| | 64x | 6746 |

In the second experiment, potential cross-tolerance to three other ACCase-inhibitor herbicides (clethodim, quizalofop, and fenoxaprop) was investigated at the 2- to 3-leaf growth stage (Table 2). The dose-response assay included seven doses for the ACCase-resistant grain sorghum (1×, 2×, 4×, 8×, 16×, 32×, and 64×) and six doses for the susceptible standard (1/32×, 1/16×, 1/8×, 1/4×, 1/2× and 1×). The field rate (1×) used were 140 g ai $ha^{-1}$ for clethodim, 112 g ai $ha^{-1}$ for quizalofop, and 87.3 g ai $ha^{-1}$ for fenoxaprop. Applications of clethodim and quizalofop included a non-ionic surfactant (0.25% v/v) and COC (1% v/v), respectively. Data were regressed using an exponential 3P curve using JMP Pro 14.2.

TABLE 2

Rates used to evaluate grain sorghum response to various ACCase-inhibitor herbicides.

| | Susceptible sorghum | | Resistant sorghum | |
|---|---|---|---|---|
| Herbicide | Rate designation | Rate (g ai $ha^{-1}$) | Rate designation | Rate (g ai $ha^{-1}$) |
| Clethodim[1] | 0.03125x | 3.78 | 1x | 140 |
| | 0.0625x | 8.75 | 2x | 280 |
| | 0.125x | 17.5 | 4x | 560 |
| | 0.25x | 35 | 8x | 1120 |
| | 0.5x | 70 | 16x | 2240 |
| | 1x | 140 | 32x | 4480 |
| | | | 64x | 8960 |
| Quizalofop[2] | 0.03125x | 3.5 | 1x | 112 |
| | 0.0625x | 7 | 2x | 224 |
| | 0.125x | 14 | 4x | 448 |
| | 0.25x | 28 | 8x | 896 |
| | 0.5x | 56 | 16x | 1792 |
| | 1x | 112 | 32x | 3584 |
| | | | 64x | 7168 |
| Fenoxaprop[2] | 0.03125x | 2.7 | 1x | 87.3 |
| | 0.0625x | 5.5 | 2x | 174.6 |
| | 0.125x | 10.9 | 4x | 349.2 |
| | 0.25x | 21.8 | 8x | 698.4 |
| | 0.5x | 43.7 | 16x | 1396.8 |
| | 1x | 87.3 | 32x | 2793.6 |
| | | | 64x | 5587.2 |

[1]Rate chosen as 1x rate labeled in soybean.
[2]Rate chosen as 1x rate labeled in rice.

Observations: Visual grain sorghum injury (%) ratings were taken at 14, 21, and 28 days after application (DAA). The ratings were on a scale of 0-100, with 0 indicating no plant injury or growth reduction compared to the non-treated standard and 100 indicating complete plant death. Plants were harvested 28 DAA and dry biomass determined after drying at 55° C. for three days. See FIG. 9-12.

Figure 9:
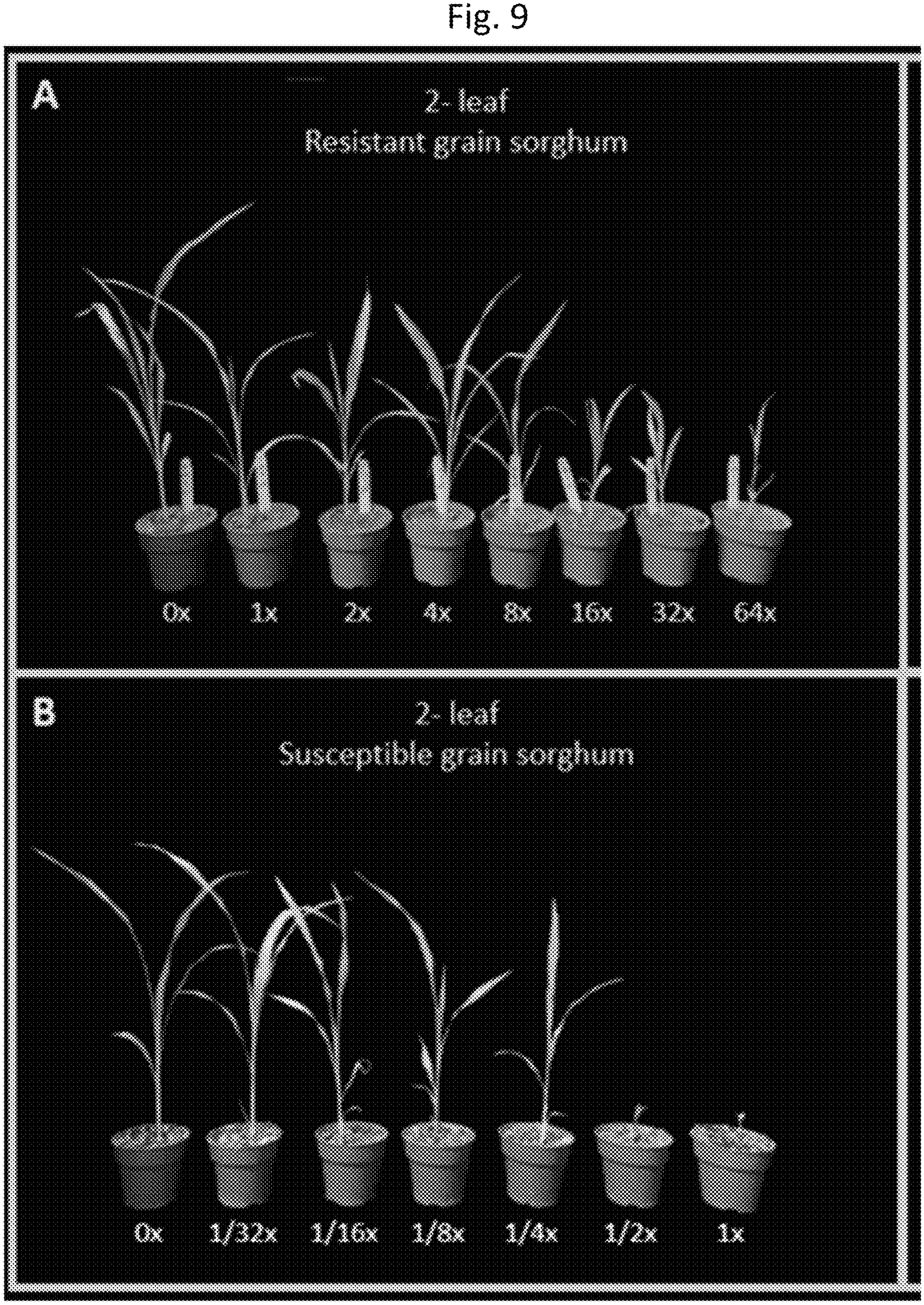
FIG. 9 shows the response of grain sorghum (GS) to fluazifop applied at three different growth stages: 2-leaf (A, B), 3- to 4-leaf (C, D), and 5- to 6-leaf (E, F). The rates of fluazifop range from 0 to 64× for resistant GS (A, C, E), and from 0 to 1× for susceptible GS (B, D, F) with 1× being 105 g ai $ha^{-1}$. Photographs were taken 28 days after application.
Figure 9:
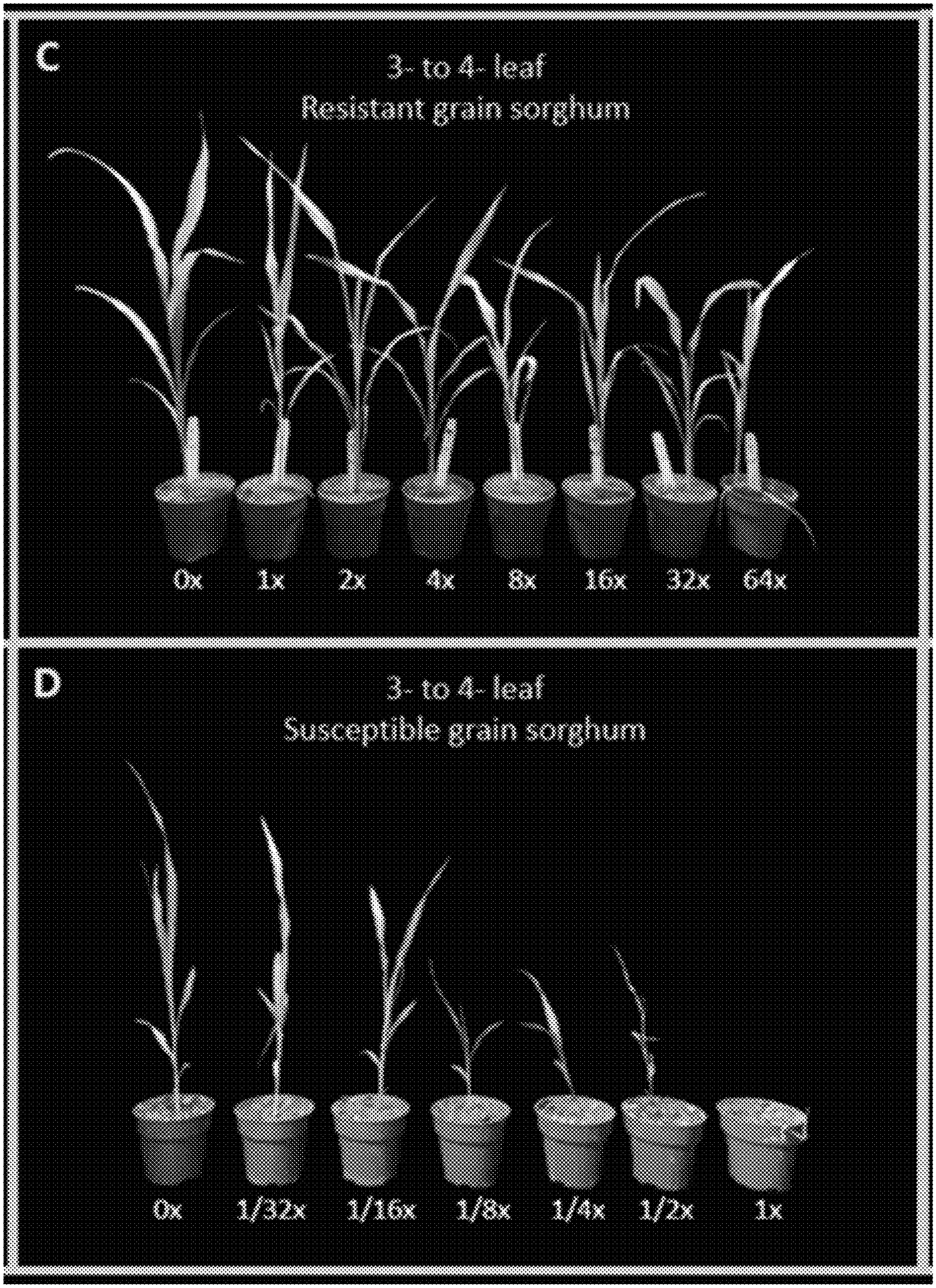
Figure 9:
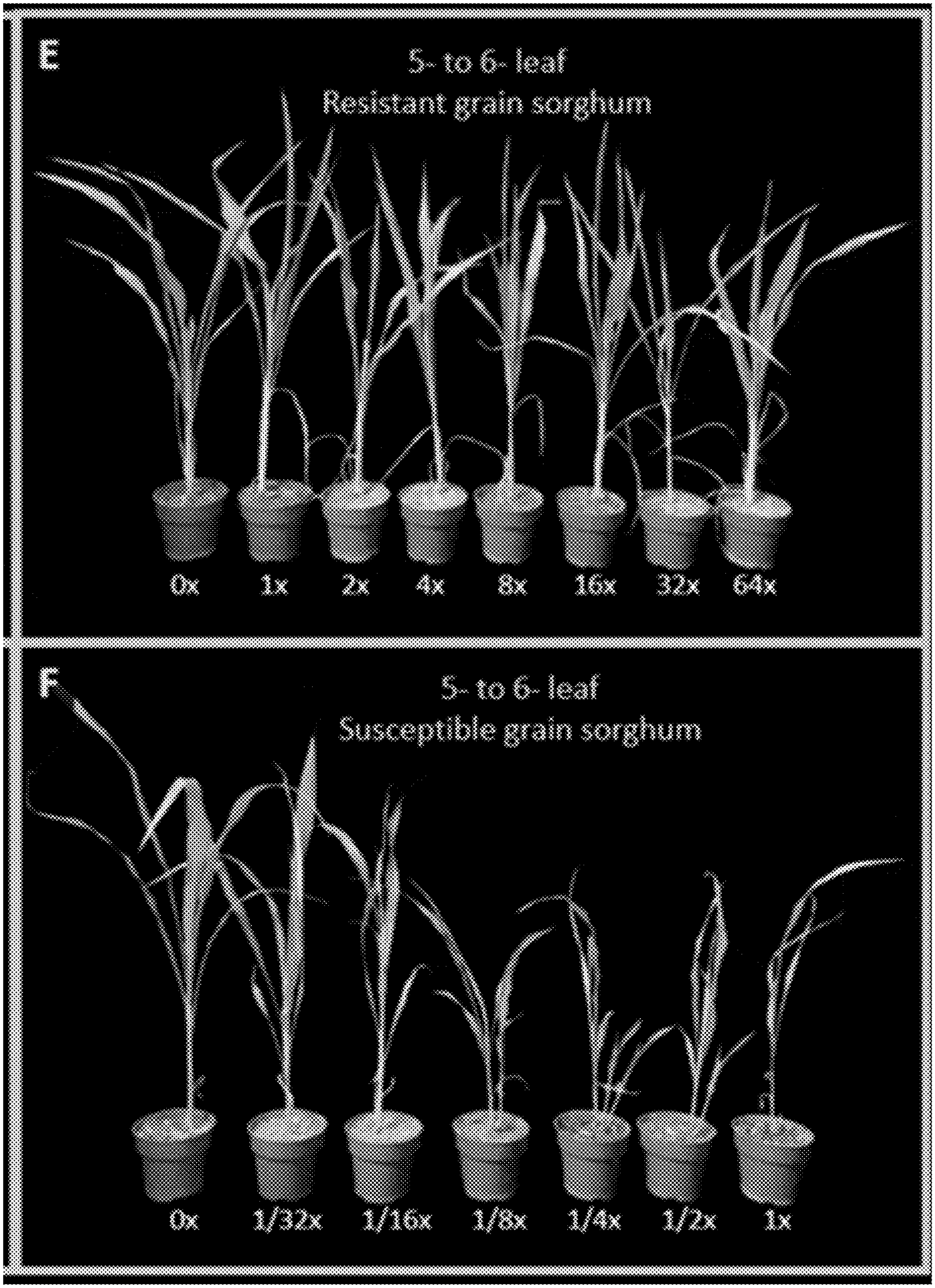
Figure 10:
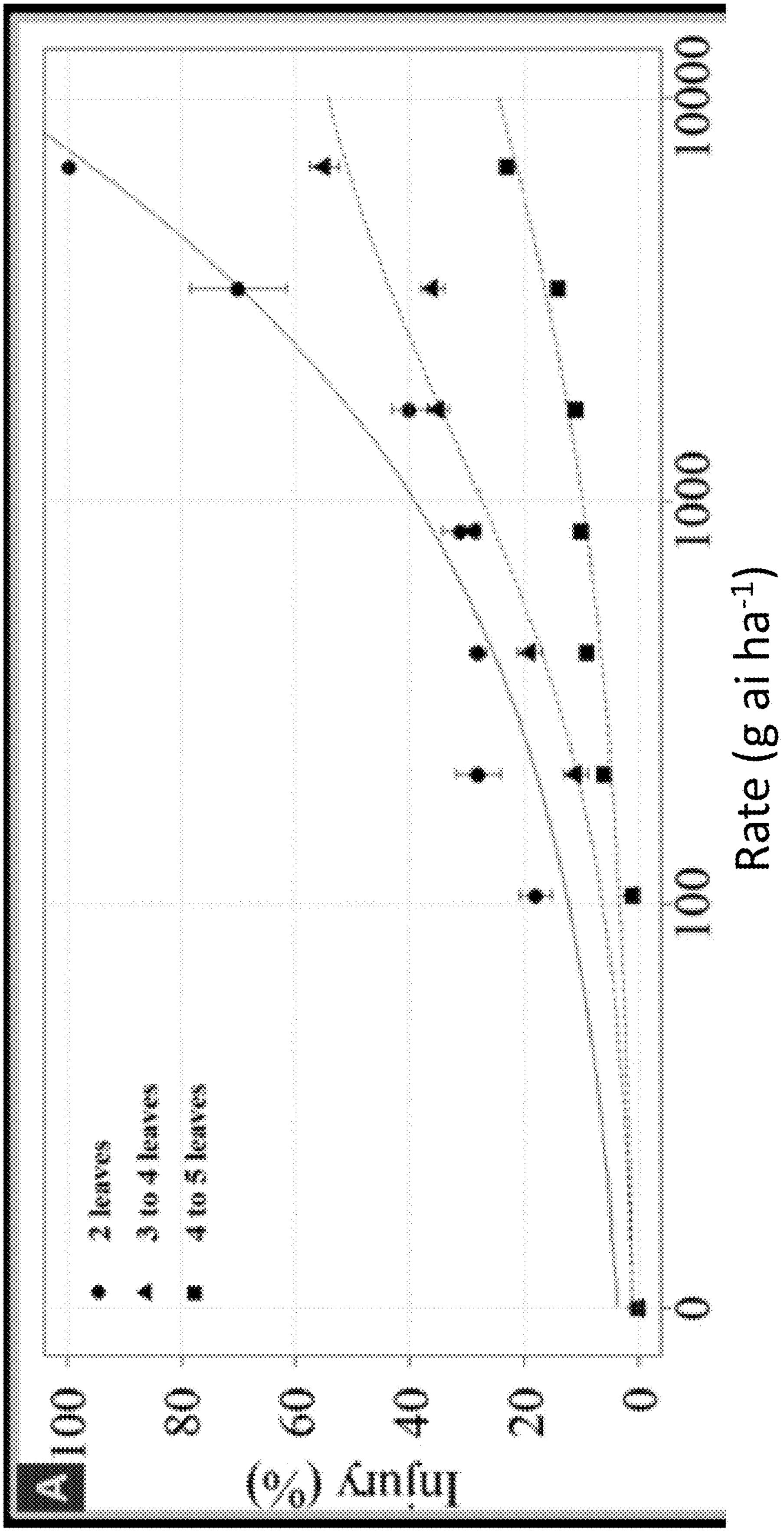
FIG. 10 shows graphs comparing the percent injury to fluazifop-resistant (A) and susceptible (B) grain sorghum caused by fluazifop. Plants were rated visually at 28 days after application. The line fit to the data is nonlinear 3P logistic curve.
Figure 10:
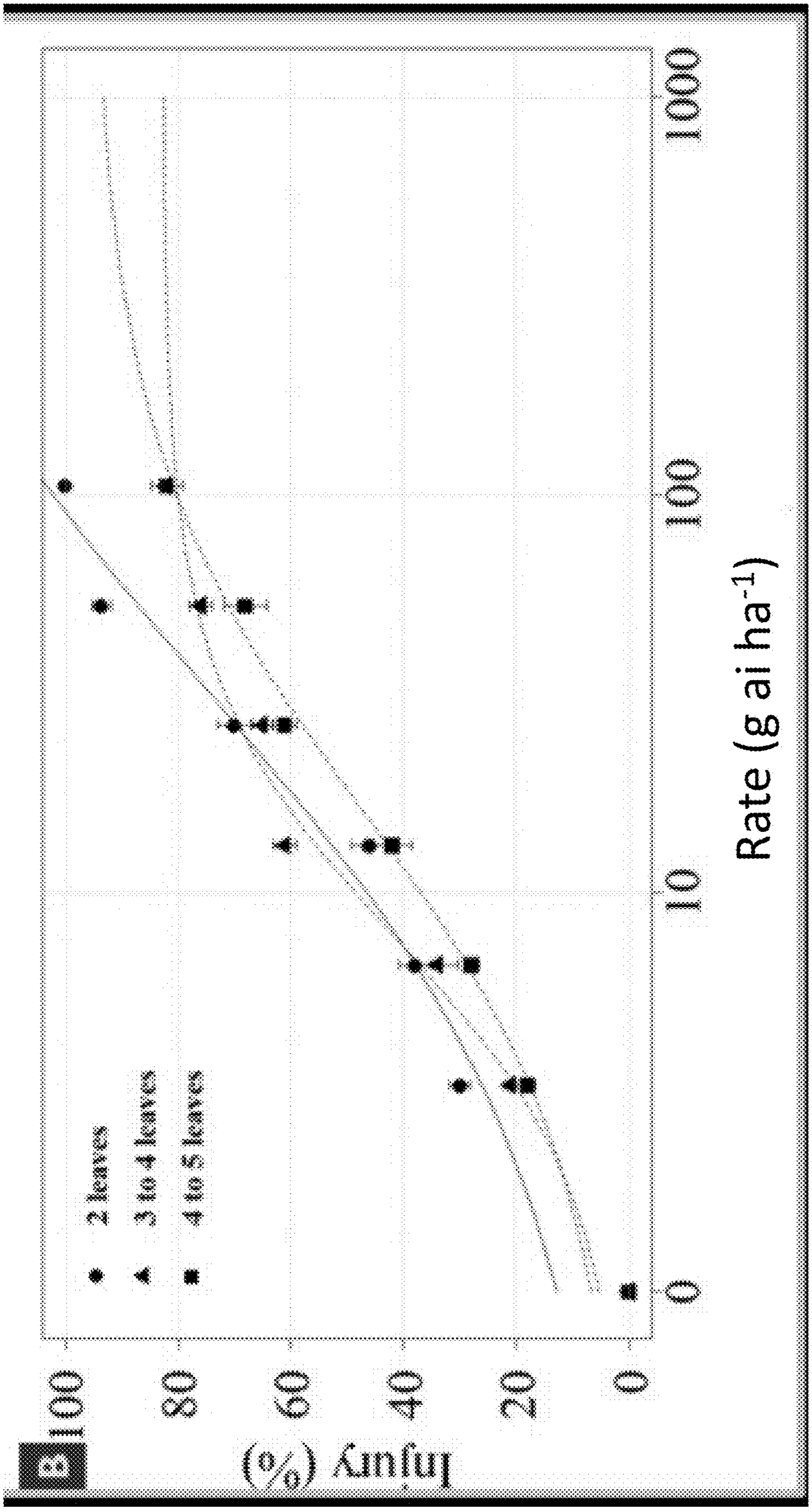
Figure 11:
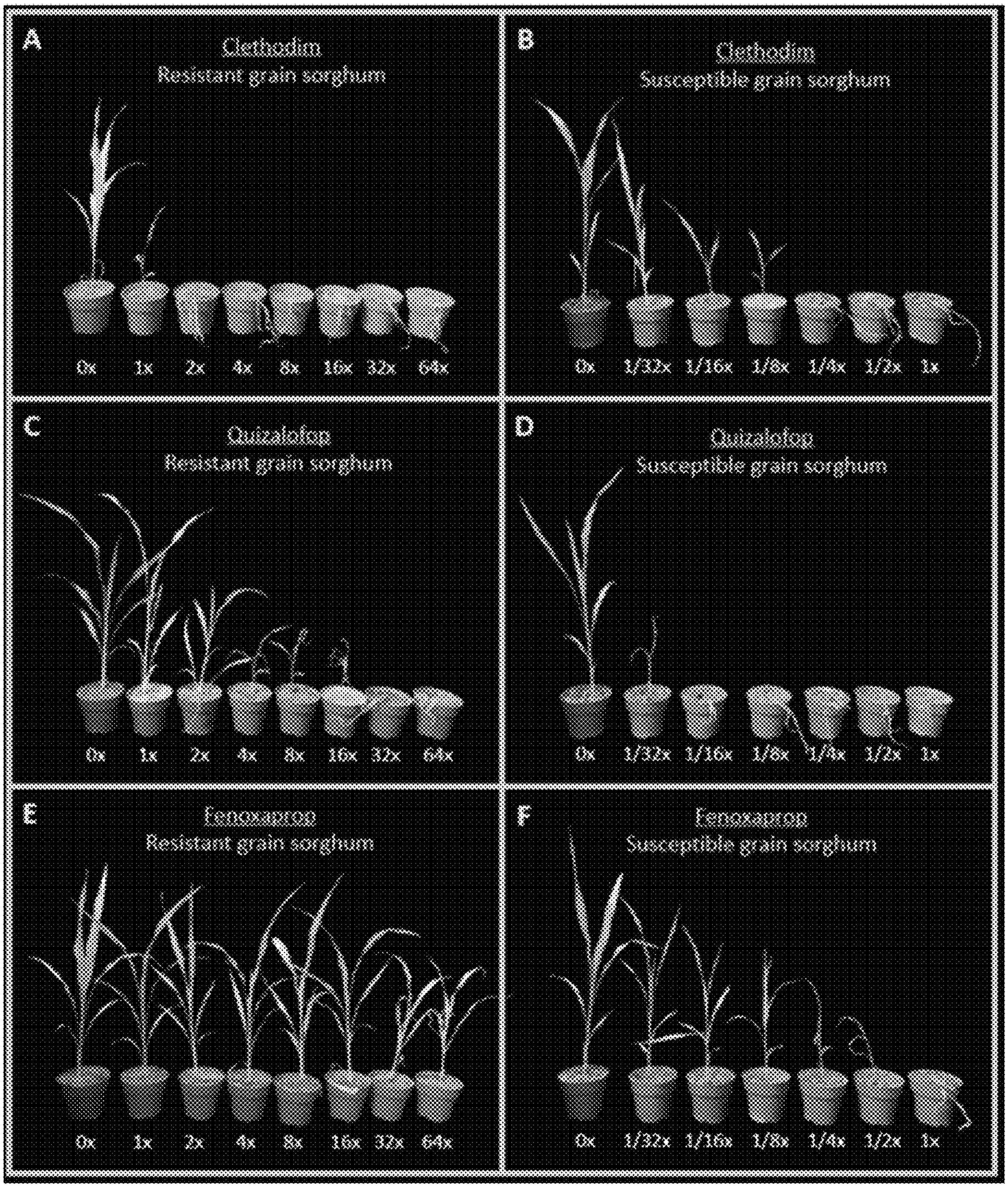
FIG. 11 shows the response of grain sorghum (GS) to rates of fluazifop ranging from 0 to 64× for resistant GS (A, C, E), and from 0 to 1× for susceptible GS (B, D, F), 28 days after application. Photographs were taken 28 days after application.
Figure 12:
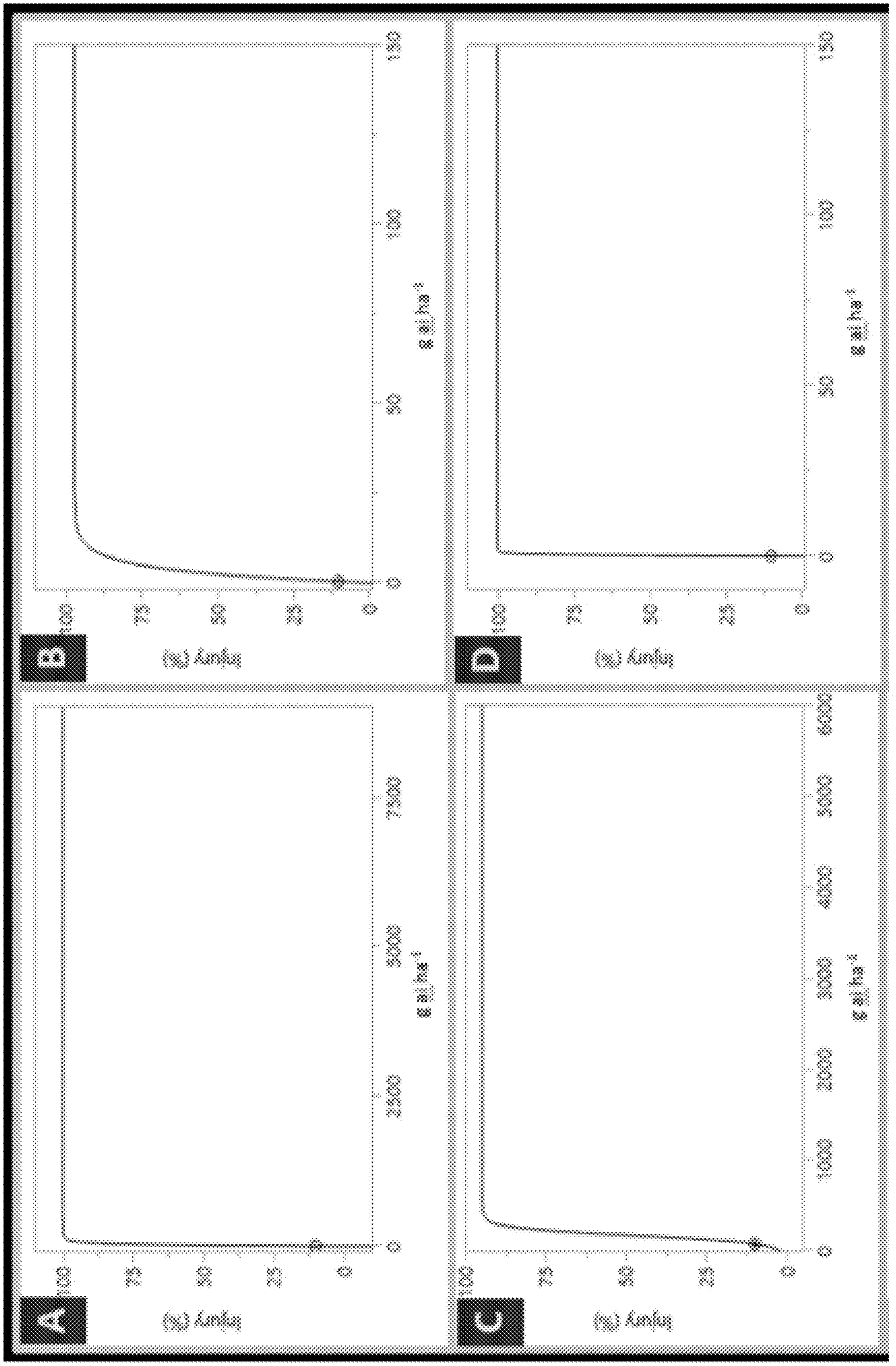
FIG. 12 shows graphs comparing the percent injury to fluazifop-resistant (A, C, E) and susceptible (B, D, F) grain sorghum (GS) caused by the ACCase-inhibiting herbicides clethodim (A, B), quizalofop (C, D), and fenoxaprop (E, F). The line fit to the data is a nonlinear Exponential 3P curve. Plants were rated visually at 28 days after application.
Figure 12:
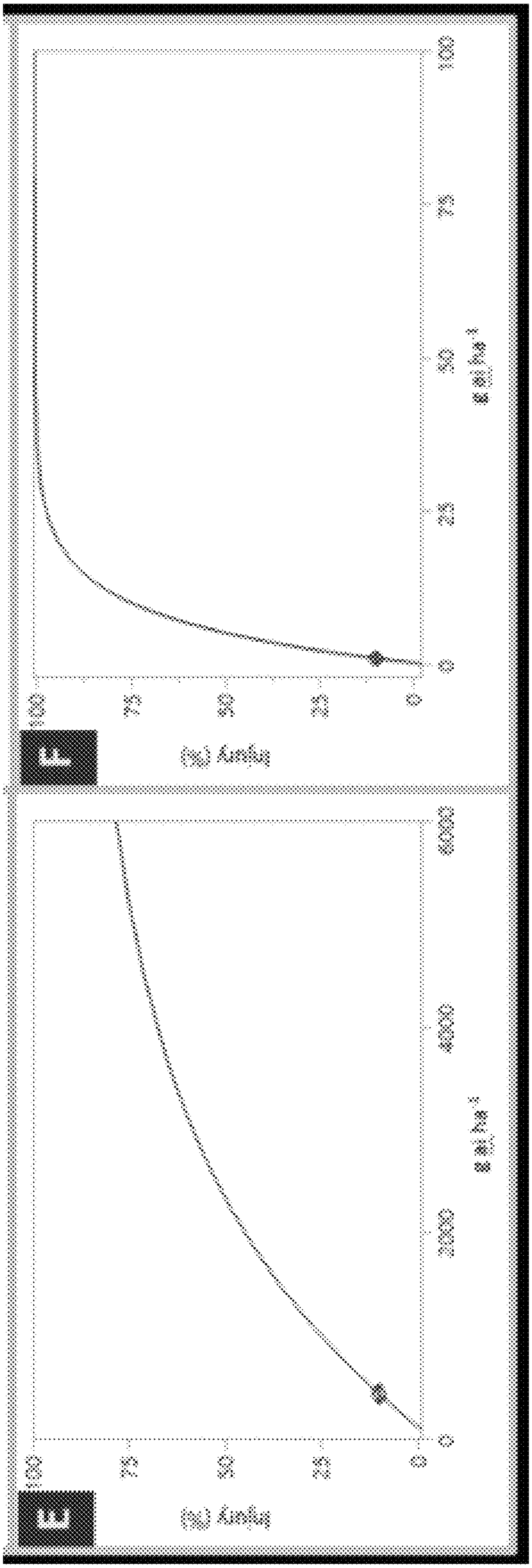

Results:

The sorghum line developed here showed commercially acceptable tolerance to fluazifop and fenoxaprop. The line also somewhat tolerated quizalofop application, but it is not commercially acceptable. It was however completely susceptible to clethodim. FIG. 9 shows a comparison of the resistant (A) and susceptible (B) sorghum lines after treatment with the herbicide at the indicated rates at the 2 leaf stage, the 3-4 leaf stage (C, resistant and D, susceptible) and 5-6 leaf stage (E, resistant and F, susceptible). FIGS. 10A (resistant) and 10B (susceptible) show comparison of plant injury to the plants after application of fluazifop at the indicated stages when applied at the indicated rates. The resistant plants have low injury rates even when the herbicide is applied at both early and late growth stages and at rates over the commercially recommended rates for control of weeds. FIGS. 11 and 12 display similar data for other related herbicides.

Identification of Target-Site Resistance Mechanism

The ACCase gene of the fluazifop-resistant sorghum line was sequenced using overlapping primers (6 primer sets) covering the 1737 bp Carboxyl Transferase (CT) domain region. The sequences of these primers are shown in Table 3.

TABLE 3

Forward (F) and reverse (R) primers used to sequence the ACCase gene of the fluazifop-resistant sorghum line.

| Primer # | Primer Name | Sequence | Product size, bp |
|---|---|---|---|
| P1 | SbACCase1-F | TGCAGCTAGA TAGCGGTGAA (SEQ ID NO: 26) | 1116 |
| | SbACCase1-R | TTATCAACTC GGGGTCAAGC (SEQ ID NO: 27) | |
| P2 | SbACCase2-F | TTGTCCCTGC TGATCCAGGT (SEQ ID NO: 28) | 400 |
| | SbACCase2-R | AACCCTTGAG GTTCGAGAAC (SEQ ID NO: 29) | |
| P3 | SbACCase3-F | TGTTGGGTGG TCTGACGAAG (SEQ ID NO: 30) | 596 |
| | SbACCase3-R | CACGTGGATC GCATGTGTTC (SEQ ID NO: 31) | |
| P4 | SbACCase4-F | TGGCTCAGCT ATGTTCCTGC (SEQ ID NO: 32) | 839 |
| | SbACCase4-R | GGCAGCAACT GTTTCGTACG (SEQ ID NO: 33) | |
| P5 | SbACCase2-F | GAAGAAGACT ATGCCCGTAT TAG (SEQ ID NO: 34) | 1091 |
| | SbACCase2-R | CCTCTGACCT GAACTTGATT T (SEQ ID NO: 35) | |
| P6 | SbACCase3-F | GAGGACTGCC AAAGGTAATG (SEQ ID NO: 36) | 624 |
| | SbACCase3-R | GAAAGACCCT GCGAGAATG (SEQ ID NO: 37) | |

The PCR reaction mix contained 2 ul DNA (10 ng), 5 ul of 10×PCR buffer, 1 ul of 10 uM dNTPs, 1 ul of both forward and reverse primer (10 μm/μl), 0.25 ul of Taq polymerase, and 37.75 ul of sterile distilled water. The PCR conditions included pre-incubation at 95° C. for 30 sec, then 30 cycles of denaturation at 95° C. for 12 sec, annealing at 58° C. for 30 sec, and extension at 72° C. for 1 min, followed by a final extension at 72° C. for 5 min. The PCR products were run on 1.2% agarose gel and the products were extracted and purified for Sanger sequencing.

Figure 13:
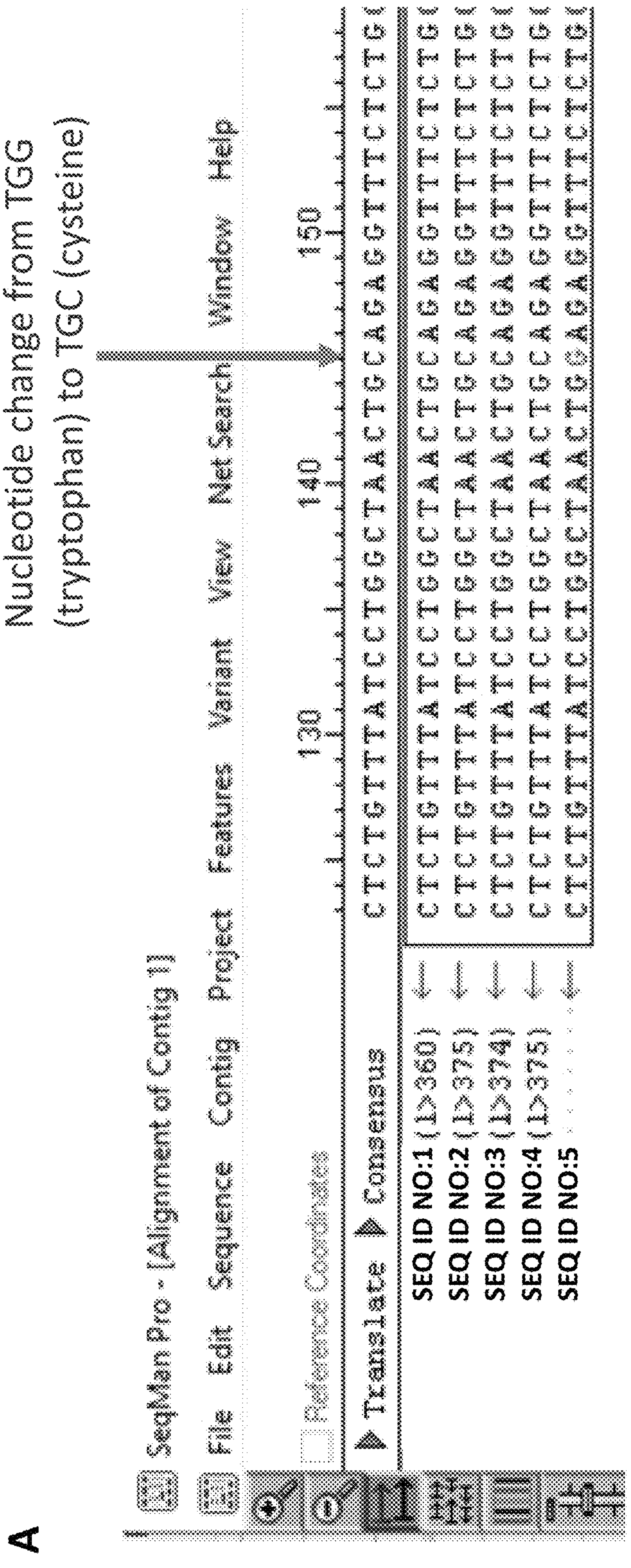
FIG. 13 shows a confirmation of target-site mutation W2031C in the fluazifop-resistant sorghum line. Panel A shows the G>C nucleotide change at residue 2031 of the ACCase gene. The sequences depicted are portions of SEQ ID NOs:1-5 that are centered on this mutation. These sequences were produced by amplifying the ACCase gene of the indicated plant using primer P2. SEQ ID NOs:1-3 are from fluazifop-resistant sorghum plants; SEQ ID NO:4 is from fluazifop-resistant johnsongrass; and SEQ ID NO:5 is from wild-type sorghum (BTx2928). Panel B shows the corresponding W>C amino acid change. The “Query” sequence (SEQ ID NO:6) is from a fluazifop-resistant sorghum plant and the “Sbjct” sequence (SEQ ID NO:7) is from wild-type sorghum.

The sequencing results were used to generate consensus sequences for the fluazifop-resistant ACCase gene (SEQ ID NO:38) and protein (SEQ ID NO:39). Two specific mutations were identified in the fluazifop-resistant sorghum line. The first mutation (FIG. 13) consisted of a change from tryptophan (W) to cysteine (C) at residue 2031 (W2031C) of the ACCase gene of the fluazifop-resistant sorghum line, which corresponds to residue 2027 of the ACCase gene in blackgrass (*Alopecurus myosuroides*). This mutation has been reported in several ACCase resistant weed species.

Figure 14:
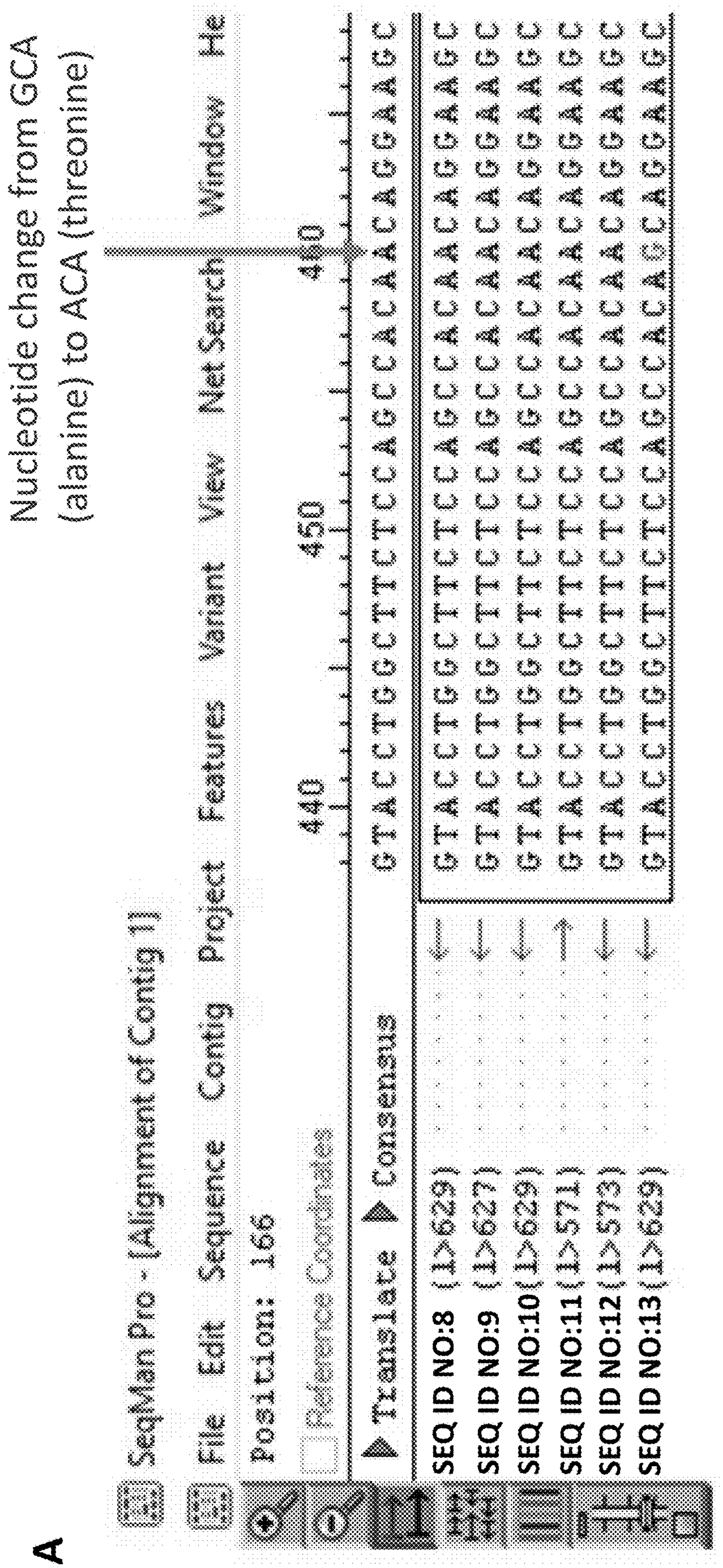
FIG. 14 shows a confirmation of target-site mutation A2248T in the fluazifop-resistant sorghum line. Panel A shows the G>A nucleotide change at residue 2248 of the ACCase gene. The sequences depicted are portions of SEQ ID NOs:8-13 that are centered on this mutation. These sequences were produced by amplifying the ACCase gene of the indicated plant using primer P6. SEQ ID NOs:8-10 are from fluazifop-resistant sorghum plants; SEQ ID NOs:11-12 are from fluazifop-resistant johnsongrass; and SEQ ID NO:13 is from wild-type sorghum (BTx2928). Panel B shows the corresponding A>T amino acid change. The “Query” sequence (SEQ ID NO:14) is from a fluazifop-resistant sorghum plant and the “Sbjct” sequence (SEQ ID NO:15) is from wild-type sorghum.

The second mutation (FIG. 14) consisted of a change from alanine (A) to threonine (T) at residue 2248 (A2248T) of the ACCase gene of the fluazifop-resistant sorghum line. Notably, this second mutation was identified outside of the region where currently known mutations have been reported.

Figure 15:
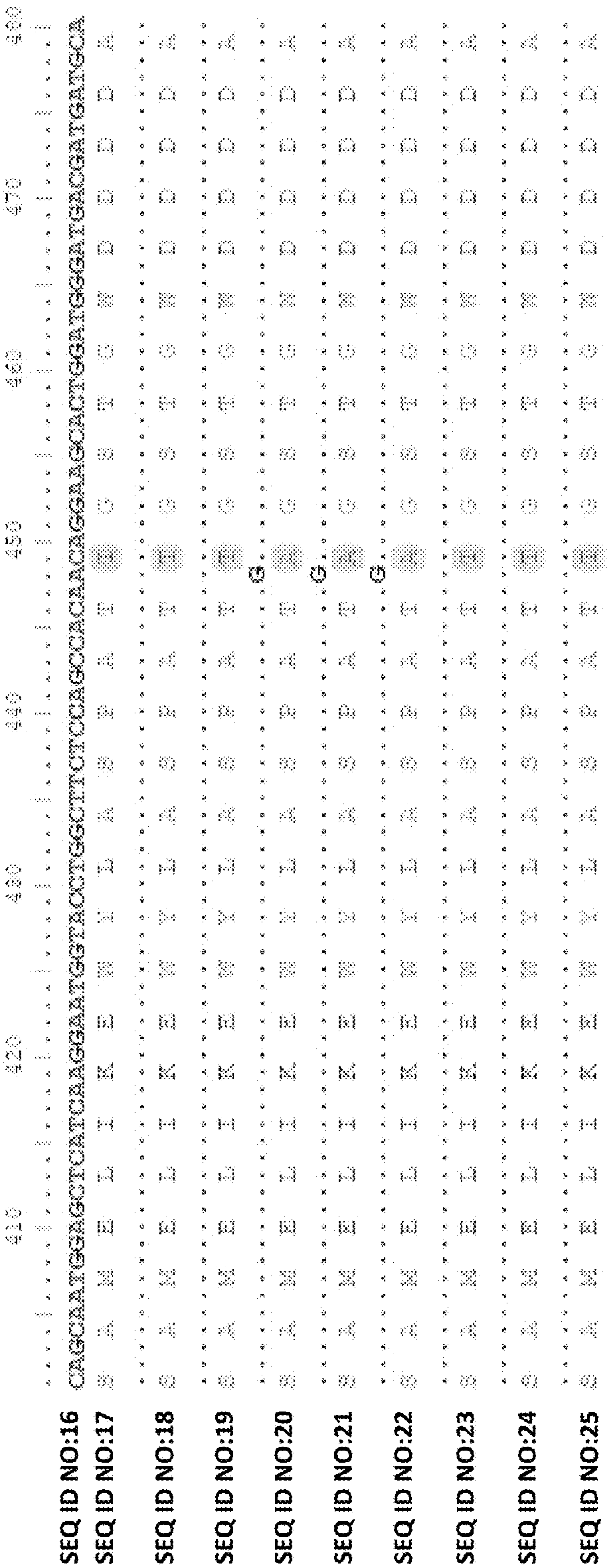
FIG. 15 shows the DNA sequence (SEQ ID NO:16) and an amino acid sequence alignment that confirms that the A2248T mutation is present in both wild-type johnsongrass (SEQ ID NOs:23-25) and fluazifop-resistant sorghum (SEQ ID NOs:17-19), but is absent in wild-type sorghum (SEQ ID NOs:20-22).

Further investigation of the second mutation (A2248T) revealed that this allele is native to the ACCase gene of johnsongrass (FIG. 15), and is absent in wild-type grain sorghum. Thus, the presence of this specific mutation confirms that the fluazifop-resistant grain sorghum developed in this research comprises an ACCase gene that originated in johnsongrass. This mutation may be used as a marker for this trait. Additional studies will be necessary to determine whether this second mutation contributes to fluazifop tolerance.

REFERENCES

Besancon T, Heiniger R, Weisz E, Everman W (2017) Weed response to agronomic practices and herbicide strategies in grain sorghum. Agron J. 109:1642-1650

Fromme D D, Dotray P A, Grichar W J, Fernandez C J (2012) Weed control and grain sorghum (*Sorghum bicolor*) tolerance to pyrasulotole plus bromoxynil. Int J Ag. doi:10.1155/2012/951454

Heap I (2020) The international survey of herbicide resistant weeds. Retrieved Wednesday, Jan. 15, 2020 Available at weedscience.org Liu W, Harrison D K, Chalipska D, Gornicki P, O'Donnell C C, Adkins S W, Haselkorn R, Williams R R (2007) Single-site mutations in the carboxyltransferase domain of plastid acetyl-CoA carboxylase confer resistance to grass-specific herbicides. PNAS. 104:3627-3632

Werle R, Jhala A J, Yerka M K, Dille J A, Lindquist J L (2016) Distribution of herbicide-resistant shattercane and johnsongrass populations in sorghum production areas of Nebraska and northern Kansas. Agron J. 108:321-328

Example 3: Characterization of the Fluazifop-Resistant Grain Sorghum Breeding Line Under Field Conditions The following Example describes experiments that were performed to evaluate the grain sorghum line disclosed herein under field conditions. Specifically, the fluazifop-resistant sorghum was tested to (1) assess cross-resistance to other ACCase-inhibiting herbicides, and (2) compare the ability of fluazifop-p-butyl to control johnsongrass to that of a standard treatment.

Evaluation of the Tolerance of the Selected Fluazifop-Resistant Grain Sorghum to an Array of ACCase-Inhibiting Herbicides Under Field Conditions Standard small-plot research plots were established in spring 2020 on 36-inch wide rows encompassing 4 rows per plot. The various herbicides and rates evaluated are listed in Table 4. Applications were made to 2- to 3-leaf grain sorghum. Crop oil concentrate at 1% v/v was applied in combination with each herbicide. All applications were made at 15 gal/acre and a speed of 3 mph using a hand-held 4-nozzle boom equipped with AIXR 110015 nozzles. Only the two center rows of each plot were treated. Injury was rated on a 0 to 100 scale at approximately 2, 3, and 4 weeks after treatment (WAT) were 0 equals no injury and 100 equals crop death. Crop height was measured approximately 4 weeks after treatment.

Results: Deeming 15% as an acceptable level of injury, the evaluated grain sorghum exhibited commercial tolerance to all individual ACCase-inhibiting herbicides, except clethodim, sethoxydim, and the 2× rate of quizalofop which caused 16% injury at 2 WAT. Of the herbicides evaluated, only clethodim and sethoxydim significantly reduced grain sorghum height. None of the herbicides evaluated, except for sethoxydim and clethodim, significantly delayed grain sorghum maturity. As shown in Table 4, this cultivar showed commercially acceptable tolerance to fluazifop (2% injury), fenoxaprop-p-ethyl (3% injury), cyhalofop-butyl (5% injury), quizalofop-p-ethyl (5% injury), clodinafop-propargyl (7% injury), pinoxaden (9% injury), diclofop-methyl (4% injury), and a combination of fluazifop and fenoxaprop (12% injury) at 2 weeks after treatment at a 1× rate of herbicide application at the 2- to 3-leaf stage (see Table 4). Treatment with many of these herbicides was also well-tolerated at higher rates as well.

TABLE 4

Injury ratings, height, and maturity of fluazifop-resistant grain sorghum in response to ACCase-inhibiting herbicides in Fayetteville, AR, in 2020.

| | | | Injury | | | | |
|---|---|---|---|---|---|---|---|
| Trade name | Common name | Rate fl oz/acre | 2 WAT[a] | 3 WAT % | 4 WAT | Height[b] cm | Relative maturity[c] days |
| None (check) | — | — | 0 | 0 | 0 | 30.8 | 0 |
| Fusilade DX | Fluazifop-p-butyl | 6 | 2 | 4 | 3 | 31.5 | −2.3 |
| | | 12 | 9 | 4 | 4 | 30.1 | 0.3 |
| | | 24 | 12 | 10 | 7 | 29.8 | −1.8 |
| Ricestar HT | Fenoxaprop-p-ethyl | 17 | 3 | 3 | 2 | 31.8 | −3.5 |
| | | 34 | 5 | 1 | 2 | 31.3 | −1.8 |
| Clincher | Cyhalofop-butyl | 15 | 5 | 8 | 6 | 29.1 | 1.3 |
| | | 30 | 7 | 10 | 9 | 30.1 | 4.0 |
| Select Max | Clethodim | 16 | 100 | 100 | 100 | 0 | — |
| | | 32 | 100 | 100 | 100 | 0 | — |
| Poast Plus | Sethoxydim | 24 | 88 | 80 | 80 | 16.6 | 7.1 |
| | | 48 | 94 | 93 | 93 | 14.0 | — |
| Assure II | Quizalofop-p-ethyl | 12 | 5 | 3 | 3 | 29.9 | −0.3 |
| | | 24 | 16 | 9 | 10 | 30.7 | −5.3 |

TABLE 4-continued

Injury ratings, height, and maturity of fluazifop-resistant grain sorghum in response to ACCase-inhibiting herbicides in Fayetteville, AR, in 2020.

| | | | Injury | | | | |
|---|---|---|---|---|---|---|---|
| Trade name | Common name | Rate fl oz/acre | 2 WAT[a] | 3 WAT % | 4 WAT | Height[b] cm | Relative maturity[c] days |
| Fusion | Fluazifop-p-butyl + Fenoxaprop-p-ethyl | 12 | 12 | 16 | 12 | 29.9 | −3.8 |
| | | 24 | 22 | 20 | 19 | 28.5 | −3.3 |
| Discover NG | Clodinafop-propargyl | 16 | 7 | 4 | 4 | 30.5 | 0.5 |
| | | 32 | 7 | 6 | 9 | 29.7 | −0.8 |
| Axial XL | Pinoxaden | 16.4 | 9 | 13 | 11 | 30.0 | −6.0 |
| | | 32.8 | 13 | 14 | 11 | 29.9 | −2.5 |
| Hoelon | Diclofop-methyl | 42.7 | 4 | 3 | 3 | 32.0 | −0.8 |
| | | 85.4 | 4 | 4 | 5 | 30.2 | 1.8 |
| LSD (0.05) | | | 8 | 7 | 6 | 2.8 | 4.5 |

[a]Abbreviation: WAT, weeks after treatment

[b]Height was measured 4 weeks after treatment

[c]Maturity was measured in days to 50% heading relative to the non-treated check.

Evaluation of the Utility of Fluazifop-p-Butyl for Johnsongrass Control in Grain Sorghum Relative to a Standard Postemergence Program of Atrazine Plus S-Metolachlor Standard small-plot research plots were established in spring 2020 on 36-inch wide rows encompassing 4 rows per plot in an area known to contain a natural population of seedling and rhizomatous johnsongrass. Herbicide treatments evaluated are provided in Table 5. Crop oil concentrate at 1% v/v was applied in combination with each herbicide. All applications were made at 15 gal/acre and a speed of 3 mph using a hand-held 4-nozzle boom equipped with AIXR 110015 nozzles. Only the two center rows of each plot were treated. Injury and johnsongrass control were rated on a 0 to 100 scale, where 0 equals no injury or control and 100 equals crop death or complete control.

Results: Fusilade® (fluazifop-p-ethyl) applied alone or with AAtrex® did not cause more than 14% injury to grain sorghum, regardless of crop size at application. The standard treatment of Aatrex+Dual II Magnum® applied to 5- to 6-leaf grain sorghum was more injurious to the crop than any Fusilade-containing treatment at 1 week after the application. Fusilade, regardless of rate, applied at the 2- to 3-leaf stage of grain sorghum provided more than 85% control of seedling and rhizomatous johnsongrass. When Fusilade applications were delayed until 5- to 6-leaf stage of grain sorghum, the highest evaluated rate was needed to control johnsongrass more than 80% through 4 weeks after treatment.

TABLE 5

Tolerance of fluazifop-resistant grain sorghum to herbicide treatments applied at the 2- to 3-leaf and 5- to 6-leaf crop stage and control of a natural population of seedling and rhizomatous johnsongrass population in Fayetteville, AR, in 2020.

| | | | Injury | | | Johnsongrass control | | |
|---|---|---|---|---|---|---|---|---|
| Treatment | Rate | Timing[a] | 1 WAT[b] | 2 WAT | 3 WAT % | 2 WAT | 3 WAT | 4 WAT |
| Aatrex + Dual II Mag.[b] | 1 qt/A + 1 pt/A | 2- to 3-lf[b] | 4 | 0 | 0 | 0 | 0 | 0 |
| Fusilade DX | 8 fl oz/A | 2- to 3-lf | 5 | 4 | 3 | 99 | 88 | 87 |
| Fusilade DX | 12 fl oz/A | 2- to 3-lf | 5 | 4 | 1 | 98 | 91 | 91 |
| Fusilade DX + Aatrex | 8 fl oz/A + 1 qt/A | 2- to 3-lf | 4 | 7 | 5 | 94 | 74 | 71 |
| Fusilade DX + Aatrex | 12 fl oz/A + 1 qt/A | 2- to 3-lf | 4 | 3 | 5 | 98 | 84 | 81 |
| Aatrex + Dual II Mag. | 1 qt/A + 1 pt/A | 5- to 6-lf | 18 | 9 | 2 | 85 | 68 | 65 |
| Fusilade DX | 8 fl oz/A | 5- to 6-lf | 6 | 8 | 2 | 82 | 58 | 55 |
| Fusilade DX | 12 fl oz/A | 5- to 6-lf | 9 | 14 | 6 | 92 | 86 | 82 |
| Fusilade DX + Aatrex | 8 fl oz/A + 1 qt/A | 5- to 6-lf | 6 | 6 | 5 | 77 | 58 | 55 |
| Fusilade DX + Aatrex | 12 fl oz/A + 1 qt/A | 5- to 6-lf | 7 | 6 | 6 | 85 | 81 | 78 |
| LSD(0.05) | | | 5 | 6 | 3 | 18 | 17 | 17 |

[a]Timing was based on grain sorghum size at application.

[b]Abbreviations: WAT, weeks after the 5- to 6-leaf application timing; lf, leaf; Mag., Magnum

DEPOSIT INFORMATION

A deposit of the sorghum cultivar '21534_ACCase-R' disclosed above and recited in the appended claims has been made with the American Type Culture Collection (ATCC), 10801 University Boulevard, Manassas, Va. 20110. The date of deposit was Oct. 3, 2022. The deposit of 625 seeds was taken from the same deposit maintained by the University of Arkansas Division of Agriculture Sorghum Research and Extension Center (2900 Hwy 130 E., Stuttgart, Ark. 72160) since prior to the filing date of this application. All restrictions will be irrevocably removed upon granting of a patent, and the deposit is intended to meet all of the requirements of 37 C.F.R. §§ 1.801-1.809. The ATCC Accession Number is PTA-127360. The deposit will be maintained in the depository for a period of thirty years, or five years after the last request, or for the enforceable life of the patent, whichever is longer, and will be replaced as necessary during that period.

What is claimed is:

1. A sorghum seed comprising a polynucleotide encoding the polypeptide of SEQ ID NO: 39.

2. The sorghum seed of claim 1, wherein the sorghum seed is of variety '21534_ACCase-R,' a representative sample of seed of said variety having been deposited under ATCC Accession No. PTA-127360.

3. A sorghum plant, or a part thereof, produced by growing the seed of claim 1, wherein the sorghum plant, or a part thereof, comprises the polynucleotide encoding the polypeptide of SEQ ID NO: 39.

4. The plant of claim 3, wherein the plant is resistant to ACCase inhibitor herbicides.

5. The plant of claim 4, wherein the ACCase inhibitor herbicide is selected from the group consisting of fluazifop-p-butyl, fenoxaprop-p-ethyl, cyhalofop-butyl, quizalofop-p-ethyl, clodinafop-propargyl, pinoxaden, diclofop-methyl, and a combination thereof.

6. The plant of claim 3, wherein the plant is photoperiod-insensitive.

7. A sorghum plant, or a part thereof, having all the physiological and morphological characteristics of the sorghum plant of claim 3.

8. Pollen or an ovule of the plant of claim 3.

9. A method for producing sorghum plants, said method comprising planting a plurality of sorghum seeds as recited in claim 1 under conditions favorable for the growth of sorghum plants.

10. The method of claim 9, wherein the sorghum plants are treated with an ACCase inhibitor herbicide, wherein the percent injury to the sorghum is preferably less than 15% following treatment with the ACCase inhibitor and wherein the control of rhizomatous johnsongrass is preferably greater than 85%.

11. The method of claim 9, further comprising the step of producing sorghum seed from the resulting sorghum plants.

12. A sorghum seed produced by the method of claim 11, wherein the sorghum seed comprises the polynucleotide encoding the polypeptide of SEQ ID NO: 39.

13. A tissue culture of regenerable cells or protoplasts produced from the sorghum plant of claim 3.

14. The tissue culture of claim 13, wherein said cells or protoplasts are produced from a tissue selected from the group consisting of embryos, meristematic cells, pollen, leaves, anthers, roots, root tips, pistils, anthers, cotyledon, hypocotyl, panicles, flowers, seeds, and stems.

15. A sorghum plant regenerated from the tissue culture of claim 13, said sorghum plant having all the morphological and physiological characteristics of '21534_ACCase-R'.

16. A method for producing a hybrid sorghum seed, said method comprising crossing a first parent sorghum plant with a second parent sorghum plant, and harvesting the resulting $F_1$ hybrid sorghum seed, wherein the first parent sorghum plant or the second parent sorghum plant is the sorghum plant of claim 3.

17. A sorghum seed produced by the method of claim 16, wherein the sorghum seed comprises the polynucleotide encoding the polypeptide of SEQ ID NO: 39.

18. The method of claim 16, wherein one of said sorghum plants is transgenic and the other is a sorghum plant of cultivar '21534_ACCase-R'.

19. The method of claim 16, further comprising the step of planting a plurality of the hybrid sorghum seed under conditions favorable for the growth of sorghum plants and optionally comprising the step of producing sorghum seed from the resulting sorghum plants.

20. A method comprising transforming the sorghum plant of claim 3 with a transgene, wherein the transgene confers at least one trait selected from the group consisting of: herbicide resistance; insect resistance; resistance to bacterial, fungal, or viral disease; modified fatty acid metabolism; modified carbohydrate metabolism; and male sterility.

21. A transgenic sorghum plant or part thereof produced by the method of claim 20.

22. A method of introducing a desired trait into sorghum cultivar '21534_ACCase-R,' said method comprising the steps of:

(a) crossing plants as recited in claim 3 with plants of another sorghum line expressing the desired trait, to produce progeny plants;

(b) selecting progeny plants that express the desired trait, to produce selected progeny plants;

(c) crossing the selected progeny plants with plants as recited in claim 3 to produce new progeny plants;

(d) selecting new progeny plants that express both the desired trait and the physiological and morphological characteristics of sorghum cultivar '21534_ACCase-R,' to produce new selected progeny plants; and (e) repeating steps (c) and (d) three or more times in succession, to produce selected higher generation backcross progeny plants that express both the desired trait and the physiological and morphological characteristics of sorghum cultivar '21534_ACCase-R,' when grown in the same environmental conditions.

23. The method of claim 22, additionally comprising the step of planting a plurality of sorghum seed produced by selecting higher generation backcross progeny plants under conditions favorable for the growth of sorghum plants and optionally comprising the step of producing sorghum seed from the resulting sorghum plants.

24. A method of growing sorghum comprising planting a seed of claim 1, applying an ACCase inhibitor herbicide and harvesting the sorghum.

25. The method of claim 24, wherein the herbicide is applied post-emergence.

* * * * *